US009738702B2

(12) United States Patent
Nesspor et al.

(10) Patent No.: US 9,738,702 B2

(45) Date of Patent: Aug. 22, 2017

(54) ANTIBODIES WITH IMPROVED HALF-LIFE IN FERRETS

(71) Applicant: Janssen Biotech, Inc., Horsham, PA (US)

(72) Inventors: Thomas Nesspor, Spring House, PA (US); Bernard Scallon, Wayne, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 14/656,149

(22) Filed: Mar. 12, 2015

(65) Prior Publication Data

US 2015/0259401 A1 Sep. 17, 2015

Related U.S. Application Data

(60) Provisional application No. 61/953,149, filed on Mar. 14, 2014.

(51) Int. Cl.
*C07K 16/10* (2006.01)

(52) U.S. Cl.
CPC ...... *C07K 16/1027* (2013.01); *C07K 2317/21* (2013.01); *C07K 2317/24* (2013.01); *C07K 2317/52* (2013.01); *C07K 2317/524* (2013.01); *C07K 2317/72* (2013.01); *C07K 2317/94* (2013.01)

(58) Field of Classification Search
CPC ............ C07K 2317/21; C07K 2317/24; C07K 2317/72; C07K 2317/52; C07K 2317/94; C07K 16/1027
USPC ..................... 530/387.3; 435/328; 536/23.53
See application file for complete search history.

(56) References Cited

U.S. PATENT DOCUMENTS

| | | | |
|---|---|---|---|
| RE30,985 | E | 6/1982 | Cartaya |
| 4,560,655 | A | 12/1985 | Baker |
| 4,657,866 | A | 4/1987 | Kumar |
| 4,767,704 | A | 8/1988 | Cleveland et al. |
| 4,816,397 | A | 3/1989 | Boss et al. |
| 4,816,567 | A | 3/1989 | Cabilly et al. |
| 4,927,762 | A | 5/1990 | Darfler |
| 4,946,778 | A | 8/1990 | Ladner et al. |
| 5,112,946 | A | 5/1992 | Malone |
| 5,122,469 | A | 6/1992 | Mather et al. |
| 5,194,594 | A | 3/1993 | Khawli et al. |
| 5,223,409 | A | 6/1993 | Ladner et al. |
| 5,255,539 | A | 10/1993 | Zimmer |
| 5,258,498 | A | 11/1993 | Huston et al. |
| 5,260,203 | A | 11/1993 | Ladner et al. |
| 5,336,603 | A | 8/1994 | Capon et al. |
| 5,349,053 | A | 9/1994 | Landolfi |
| 5,359,046 | A | 10/1994 | Capon et al. |
| 5,403,484 | A | 4/1995 | Ladner et al. |
| 5,427,908 | A | 6/1995 | Dower et al. |
| 5,447,851 | A | 9/1995 | Beutler et al. |
| 5,455,030 | A | 10/1995 | Ladner et al. |
| 5,516,637 | A | 5/1996 | Huang et al. |
| 5,530,101 | A | 6/1996 | Queen et al. |
| 5,534,411 | A | 7/1996 | Weltzin |
| 5,565,332 | A | 10/1996 | Hoogenboom et al. |
| 5,571,698 | A | 11/1996 | Ladner et al. |
| 5,580,717 | A | 12/1996 | Dower et al. |
| 5,585,089 | A | 12/1996 | Queen et al. |
| 5,622,929 | A | 4/1997 | Willner et al. |
| 5,658,727 | A | 8/1997 | Barbas et al. |
| 5,698,426 | A | 12/1997 | Huse |
| 5,723,125 | A | 3/1998 | Chang et al. |
| 5,733,743 | A | 3/1998 | Johnson et al. |
| 5,747,654 | A | 5/1998 | Pastan et al. |
| 5,750,753 | A | 5/1998 | Kimae et al. |
| 5,780,225 | A | 7/1998 | Wigler et al. |
| 5,783,181 | A | 7/1998 | Browne et al. |
| 5,807,715 | A | 9/1998 | Morrison et al. |
| 5,821,047 | A | 10/1998 | Garrard et al. |
| 5,844,096 | A | 12/1998 | Hinrichs et al. |
| 5,856,456 | A | 1/1999 | Whitlow et al. |
| 5,908,626 | A | 6/1999 | Chang et al. |
| 5,939,598 | A | 8/1999 | Kucherlapati et al. |
| 5,969,108 | A | 10/1999 | McCafferty et al. |
| 7,083,784 | B2 * | 8/2006 | Dall'Acqua ..... A61K 47/48507 424/130.1 |
| 7,658,921 | B2 * | 2/2010 | Dall'Acqua ........... C07K 16/00 424/139.1 |
| 7,704,497 | B2 * | 4/2010 | Dall'Acqua ..... A61K 47/48507 424/130.1 |
| 7,955,590 | B2 | 6/2011 | Gillies et al. |

(Continued)

FOREIGN PATENT DOCUMENTS

| | | |
|---|---|---|
| EP | 0 239 400 | 9/1987 |
| EP | 0 519 596 | 12/1992 |

(Continued)

OTHER PUBLICATIONS

Nesspor et al. Influenza Other Respir Viruses. Sep. 2014;8(5):596-604. doi: 10.1111/irv.12273. Epub Jul. 30, 2014.*

Vafa et al. Methods. Jan. 1, 2014;65(1):114-26. doi: 10.1016/j.ymeth.2013.06.035. Epub Jul. 17, 2013.*

Ames, et al., "Conversion of murine Fabs isolated from a combinatorial phage display library to full length immunoglobulins," Journal of Immunological Methods, 184: 177-186 (1995).

Barnes, et al., "Methods for Growth of Cultured Cells in Serum-Free Medium," Analytical Biochemistry, 102: 255-270 (1980).

Better, et al., *Escherichia coli* Secretion of an Active Chimeric Antibody Fragment, Science, 240: 1041-1043 (1988).

Bird, et al., "Single-Chain Antigen-Binding Proteins," Science, 242: 423-426 (1988).

Bossart, et al., "A Neutralizing Human Monoclonal Antibody Protects against Lethal Disease In a New Ferret Model of Acute Nipah Virus Infection," PLOS Pathology, 5(10): e10000642 (2009).

(Continued)

*Primary Examiner* — Lynn Bristol

(74) *Attorney, Agent, or Firm* — Eric Dichter

(57) ABSTRACT

The antibodies, immunoglobulin constructs, or immunoglobulin fusion proteins whose in vivo half-life is increased in ferrets by a modified ferret IgG Fc region can be useful to test therapeutics in ferrets and ferret models.

6 Claims, 7 Drawing Sheets

(56) References Cited

U.S. PATENT DOCUMENTS

| | | | | |
|---|---|---|---|---|
| 8,012,476 | B2 * | 9/2011 | Dall'Acqua | A61K 47/48507 424/130.1 |
| 8,323,962 | B2 * | 12/2012 | Dall'Acqua | A61K 47/48507 435/320.1 |
| 8,475,792 | B2 * | 7/2013 | Dall'Acqua | A61K 47/48507 424/130.1 |
| 8,795,661 | B2 * | 8/2014 | Dall'Acqua | A61K 47/48507 424/130.1 |
| 2006/0228332 | A1 | 10/2006 | Gillies et al. | |
| 2007/0122403 | A1 * | 5/2007 | Dall'Acqua | A61K 47/48507 424/133.1 |
| 2008/0181887 | A1 * | 7/2008 | Dall-Acqua | C07K 16/00 424/133.1 |
| 2010/0143254 | A1 * | 6/2010 | Dall'Acqua | C07K 16/1027 424/9.1 |
| 2010/0189718 | A1 * | 7/2010 | Dall'Acqua | A61K 47/48507 424/133.1 |
| 2011/0311454 | A1 * | 12/2011 | Dall'Acqua | A61K 47/48507 424/9.1 |
| 2012/0070447 | A1 * | 3/2012 | Young | C07K 16/1027 424/159.1 |
| 2013/0052135 | A1 * | 2/2013 | Dall'Acqua | A61K 47/48507 424/9.1 |
| 2013/0247236 | A1 | 9/2013 | McWhirter et al. | |
| 2013/0272964 | A1 * | 10/2013 | Dall'Acqua | A61K 47/48507 424/9.1 |
| 2014/0072958 | A1 | 3/2014 | Nabel et al. | |
| 2014/0377181 | A1 * | 12/2014 | Dall'Acqua | A61K 47/48507 424/9.1 |

FOREIGN PATENT DOCUMENTS

| | | | |
|---|---|---|---|
| EP | 0 592 106 | | 4/1994 |
| WO | WO 87/00195 | | 1/1987 |
| WO | WO 90/02809 | A1 | 3/1990 |
| WO | WO 90/03430 | | 4/1990 |
| WO | WO 91/09967 | | 7/1991 |
| WO | WO 91/10737 | A1 | 7/1991 |
| WO | WO 92/01047 | A1 | 1/1992 |
| WO | WO 92/18619 | A1 | 10/1992 |
| WO | WO 92/22324 | A1 | 12/1992 |
| WO | WO 93/11236 | A1 | 6/1993 |
| WO | WO 94/11026 | A2 | 5/1994 |
| WO | WO 94/13804 | A1 | 6/1994 |
| WO | WO 95/15982 | A2 | 6/1995 |
| WO | WO 95/20401 | A1 | 8/1995 |
| WO | WO 03/011161 | A1 | 2/2003 |
| WO | WO 2010/080538 | A1 | 7/2010 |

OTHER PUBLICATIONS

Brinkmann, et al., "Phage display of disulfide-stabilized Fv fragments," Journal of Immunological Methods, 182: 41-50 (1995).

Burton, et al., "Human Antibodies from Combinatorial Libraries," Advances in Immunology, 57: 191-280 (1994).

Dipalma, et al., "M3YD79," www.uniprot.org/uniprot/M3YD79 (May 14, 2015).

Friesen, et al., "New Class of Monoclonal Antibodies against Severe Influence: Prophylactic and Therapeutic Efficacy in Ferrets," PLoS One, 5(2): e9106, 1-7 (2010).

Gillies, et al., "High-level expression of chimeric antibodies using adapted cDNA variable region cassettes," Journal of Immunological Methods, 125: 191-202 (1989).

Ham, et al., "Media and Growth Requirements," Methods in Enzymology, 58: 44-93 (1979).

Holliger, et al., ""Diabodies": Small bivalent and bispecific antibody fragments," Proceedings of the National Academy of Science USA, 90: 6444-6448 (1993).

Hu, et al., "Minibody: A Novel Engineered Anti-Carcinoembryonic Antigen Antibody Fragment (Single-Chain Fv-$C_H3$) Which Exhibits Rapid, High-Level Targeting of Xenografts," Cancer Research, 56: 3055-3061 (1996).

Huston, et al., "Protein engineering of antibody binding sites: Recovery of specific activity in an anti-digoxin single-chain Fv analogue produced in *Escherichia coli*," Proceedings of the National Academy of Science USA, 85: 5879-5883 (1988).

Huston, et al., "Protein Engineering of Single-Chain Fv Analogs and Fusion Proteins," Antibodies and Antigens, 203: 46-88 (1991).

Jones, et al., "Replacing the Complementarity-determining regions in a human antibody with those from a mouse," Nature, 321: 522-525 (1986).

Kettleborough, et al., "Isolation of tumor cell-specific-single-chain Fv from immunized mice using phage-antibody libraries and the re-construciton of whole antibodies from these antibody fragments," European Journal of Immunology, 24: 952-958 (1994).

Kim, et al., "Identifying amino acid residues that influence plasma clearance of murine IgG1 fragments by site-directed mutagenesis," European Journal of Immunology, 24: 542-548 (1994).

Kunkel, et al, "Rapid and Efficient Site-Specific Mutagenesis without Phenotypic Selection," Methods in Enzymology, 154: 367-382 (1987).

Lin, et al., "Preclinical Pharmacokinetics, Interspecies Scaling, and Tissue Distribution of a Humanized Monoclonal Antibody against Vascular Endothelial Growth Factor," The Journal of Pharmacology and Experimental Therapeutics, 288(1): 371-378 (1999).

Maher, et al., "The Ferret: An Animal Model to Study Influenza Virus," Lab Animal, 33(9): 50-53 (2004).

Scott F. Michael, "Mutagenesis by Incorporation of a Phosphofylated Oligo During PCR Amplification," BioTechniques, 16(3): 410-412 (1994).

Mullinax, et al., "Expression of a Heterodimeric Fab Antibody Protein in One Cloning Step," BioTechniques, 12(6): 864-869 (1992).

Nesspor, et al., "Chimeric antibodies with extended half-life in ferrets," Influenza and Other Respiratory Viruses, 8: 596-604 (2014).

Oi, et al., "Chimeric Antibodies," BioTechniques, 4(3): 214-221 (1986).

Eduardo A. Padlan, "A Possible Procedure for Reducing the Immunogenicity of Antibody Variable Domains While Preserving Their Ligand-Binding Properties," Molecular Immunology, 28(4/5): 489-498 (1991).

Persic, et al., "An integrated vector system for the eukaryotic expression of antibodies or their fragments after selection from phage display libraries," Gene, 187: 9-18 (1997).

Petkova, et al., "Enhanced half-life of genetically engineered human IgG1 antibodies in a humanized FcRn mouse model: potential application in humorally mediated autoimmune disease," International Immunology, 18(12): 1759-1769 (2006).

Andreas Plückthun, "Mono-and Bivalent Antibody Fragments Produced in *Escherichia coli*: Engineering, Folding and Antigen Binding," Immunological Reviews, 130: 151-188 (1992).

Queen, et al., "A humanized antibody that binds to the interleukin 2 receptor," Proceedings of the National Academy of Science USA, 86: 10029-10033 (1989).

Reichmann, et al., "Reshaping human antibodies for therapy," Nature, 332: 323-327 (1988).

Reiter, et al., "Engineering antibody Fv fragments for cancer detection and therapy: Disulfide-stabilized Fv fragments," Nature Biotechnology, 14: 1239-1245 (1996).

Sawai, et al., "Direct Production of the Fab Fragment Derived From the Sperm Immobilizing Antibody Using Polymerase Chain Reaction and cDNA Expression Vectors," American Journal of Reproductive Immunology, 34: 26-34 (1995).

Shu, et al., "Secretion of a single-gene-encoded immunoglobulin from myeloma cells," Proceedings of the National Academy of Science USA, 90: 7995-7999 (1993).

Arne Skerra, "Bacterial expression of immunoglobulin fragments," Current Opinion in Immunology, 5: 256-262 (1993).

Studnicka, et al., "Human-engineered monocalonal antibodies retain full specific binding activity by preserving non-CDR complementarity-modulating residues," Protein Engineering, 7(6): 805-814 (1994).

(56) References Cited

OTHER PUBLICATIONS

Tomic, et al., "A rapid and simple method for introducing specific mutations into any position of DNA leaving all other positions unaltered," Nucleic Acids Research, 18(6): 1656 (1987).
Tomlinson, et al., "Methods for Generating Multivalent and Bispecific Antibody Fragments," Methods in Enzymology, 326: 461-479 (2000).
Upender, et al., "Megaprimer Method for in Vitro Mutagenesis Using Parallel Templates," BioTechniques, 18(1): 29-30 (1995).
Van der Laan, et al., "Animal models in influenza vaccine testing," Expert Review of Vaccines, 7(6): 784-793 (2008).
Verhoeyen, et al., "Reshaping Human Antibodies: Grafting an Antilysozyme Activity," Science, 239: 1534-1536 (1988).
Ward, et al., "Binding activities of a repertoire of single immunoglobulin variable domains secreted from *Escherichia coli*,".
Zoller, et al., "Oligonucleotide-directed mutagenesis using M13-derived vectors: an efficient and general procedure for the production of point mutations in any fragment of DNA," Nucleic Acids Research, 10(20): 6487-6500 (1982).

* cited by examiner

| | R00364 | R00365 | R00366 | R00367 |
|---|---|---|---|---|
| Half Life (Slow) | 31.41 | 33.22 | 41.04 | 17.24 |

| | R00372 | R00373 | R00374 | R00375 |
|---|---|---|---|---|
| Half Life (Slow) | 89.97 | 64.44 | 87.73 | 45.94 |

Figure 3

Heavy Chain

```
                                      1                                                50
EZ459103 partial ferret IgG    (1)   ------------------------------------VTVSWNSGSLTSCV
         Cloned Ferret IgG     (1)   ASTTAPSVFPLAPSCGATPGSTVALACLVSGYFPEPVTVSWNSGSLTSGV
         Mink IgG AAA51281     (1)   ASTTAPSVFPLAPSCGATPGPTVALACLVSGYFPEPVTVSWNSGSLTSCV

                                      51                                              100
EZ459103 partial ferret IgG   (15)   HTFPSVLQSSGLYSLSSMVTVPSSRWPSDTFICTVAHPASNTKVDKRVIQ
         Cloned Ferret IgG    (51)   HTFPSVLQSSGLYSLSSMVTVPSSRWPSDTFICTVAHPASNTKVDKRVIQ
         Mink IgG AAA51281    (51)   HTFPSVLQSSGLYSLSSMVTVPSSRWPSDTFICTVAHPASNTRVDKRVP-

                                      101                                             150
EZ459103 partial ferret IgG   (65)   RGPTHTDPCKNCPQPPACDMLGGPSVFMFPPKPKDTLSISRTPEVTCMVV
         Cloned Ferret IgG   (101)   GGPPHTDPCKKCPQPPACDMLGGPSVFMFPPKPKDTLSISRTPEVTCMVV
         Mink IgG AAA51281   (100)   --PGKIPPPCTCPPRAECDMLGGPSVFMFPPKPRDTLSISRTPEVTCMVV

                                      151                                             200
EZ459103 partial ferret IgG  (115)   DLEDPEVQISWFVDNQEVHAAKTNSREQQFNSTFRVVSVLPIQHQDWLKG
         Cloned Ferret IgG   (151)   DLEDPEVQISWFVDNQEVHAAKTNSREQQFNSTFRVVSVLPIQHQDWLKG
         Mink IgG AAA51281   (148)   DLEDPEVQISWFVDNQEMHTAKTNSREQQFNSTFRVVSVLPIQHQDWLKG

                                      201                                             250
EZ459103 partial ferret IgG  (165)   KVFKCKVNNKALPSPIERTISKARGEPHQPSVYVLPPPRDEMSRTTISVT
         Cloned Ferret IgG   (201)   KVFKCKVNNKALPSPIERTISKARGEPHQPSVYVLPPPRDEMSRTTISVT
         Mink IgG AAA51281   (198)   KVFKCKVNNKALPSPIERTISKVKGEAHQPSVYVLPPSRDELSKNRVSVT

                                      251                                             300
EZ459103 partial ferret IgG  (215)   CLVKDFYPPDIDVEWQSNGRQLPEASVRTTPPQLDADGSYFL--------
         Cloned Ferret IgG   (251)   CLVKDFYPPDIDVEWQSNGRQLPEASVRTTPPQLDADGSYFLYSKLSVDK
         Mink IgG AAA51281   (248)   CMVKDFYPPDIDVEWQSNGQQFPEASVRTTPPQLDADGTYFLYSKLSVDK

                                      301                              334
EZ459103 partial ferret IgG  (257)   ----------------------------------
         Cloned Ferret IgG   (301)   AHWQRGDTFTCAVLHEALHNHHTQKSISQSPGK-
         Mink IgG AAA51281   (298)   ARWQGGETFTCAVLHEALHNHHTQKTISQSPGK-
```

Light Chain

```
                                         1                                                50
EZ457190 partial ferret kappa     (1)   NDAQPSVFLFQPSPDQLHTGSASVVCMLNGFYPREVNVKWKVDGVTKNTG
         Cloned Ferret Kappa      (1)   NDAQPSVFLFQPSPDQLHTGSASVVCMLNGFYPREVNVKWKVDGVTKNTG
         Mink Kappa AAC37305      (1)   NDAQPSVFLFQPSQDQLHTGSASVVCLLNGFYPKEVTVKWMVDGVTKNTG

                                         51                                              100
EZ457190 partial ferret kappa    (51)   ILESVTEQDSKDSTYSLSSTLTMPSTEYLSHEKYSCEV------------
         Cloned Ferret Kappa     (51)   ILESVTEQDSKDSTYSLSSTLTMPSTEYLSHEKYSCEVTHKSLSSPLVKS
         Mink Kappa AAC37305     (51)   ILESVTEQDSKDSTYSLSSTLTIPSTEYLSHETYSCEVTHKSLSSPLVKS

                                         101
EZ457190 partial ferret kappa    (89)   --------
         Cloned Ferret Kappa    (101)   FQRSECQ-
         Mink Kappa AAC37305    (101)   FQRSECQ-
                   Consensus    (101)   FQRSECQ
```

Figure 6A
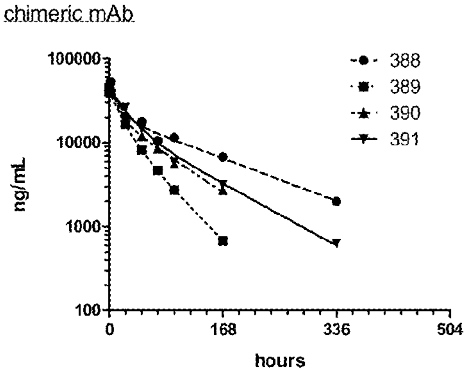
| | 388 | 389 | 390 | 391 |
|---|---|---|---|---|
| Half Life (Slow) | 99.57 | 36.12 | 55.31 | 68.50 |
Figure 6B
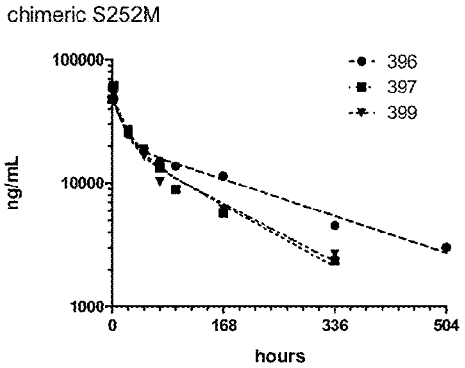
| | 396 | 397 | 399 |
|---|---|---|---|
| Half Life (Slow) | 170.8 | 101.8 | 108.1 |
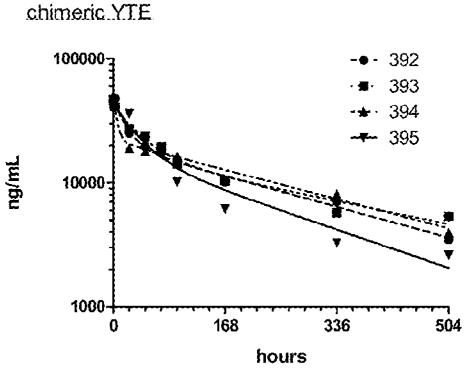
| | 392 | 393 | 394 | 395 |
|---|---|---|---|---|
| Half Life (Slow) | 203.8 | 271.0 | 214.4 | 164.5 |
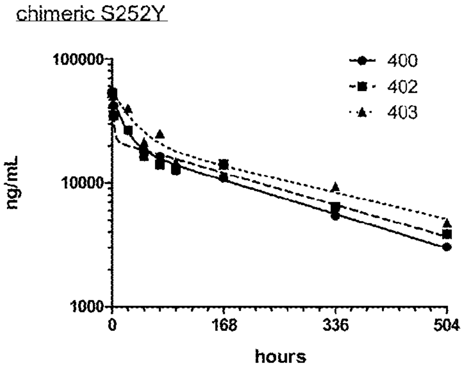
| | 400 | 402 | 403 |
|---|---|---|---|
| Half Life (Slow) | 184.5 | 196.4 | 237.7 |
Figure 6C
Figure 6D Figure 7A
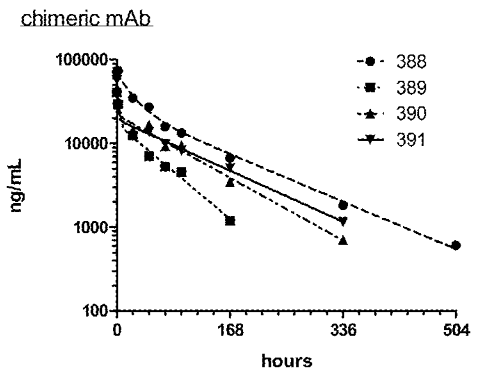
| | 388 | 389 | 390 | 391 |
|---|---|---|---|---|
| Half Life (Slow) | 88.97 | 44.56 | 67.46 | 82.82 |
Figure 7B
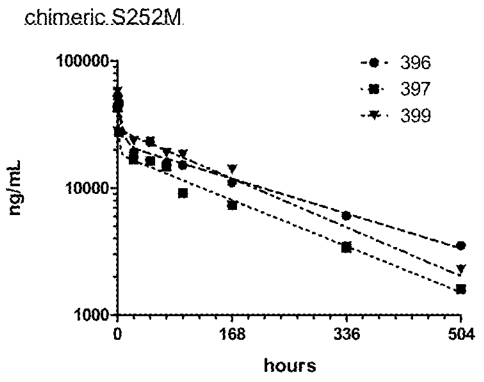
| | 396 | 397 | 399 |
|---|---|---|---|
| Half Life (Slow) | 184.3 | 139.2 | 131.5 |
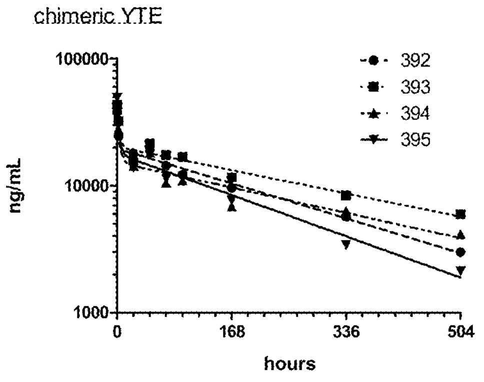
| | 392 | 393 | 394 | 395 |
|---|---|---|---|---|
| Half Life (Slow) | 184.0 | 276.2 | 253.8 | 155.5 |
Figure 7C
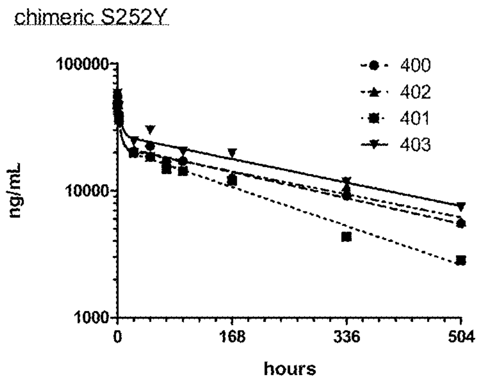
| | 400 | 401 | 402 | 403 |
|---|---|---|---|---|
| Half Life (Slow) | 247.7 | 165.0 | 279.2 | 272.9 |
Figure 7D

SEQUENCE LISTING

<160> NUMBER OF SEQ ID NOS: 10

<210> SEQ ID NO 1
<211> LENGTH: 333
<212> TYPE: PRT
<213> ORGANISM: Mustela putorius furo

<400> SEQUENCE: 1

```
Ala Ser Thr Thr Ala Pro Ser Val Phe Pro Leu Ala Pro Ser Cys Gly
1               5                   10                  15

Ala Thr Pro Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Asp Thr
65                  70                  75                  80

Phe Ile Cys Thr Val Ala His Pro Ala Ser Asn Thr Lys Val Asp Lys
                85                  90                  95

Arg Val Thr Gln Gly Gly Pro Pro His Thr Asp Pro Cys Lys Lys Cys
            100                 105                 110

Pro Gln Pro Pro Ala Cys Asp Met Leu Gly Gly Pro Ser Val Phe Met
        115                 120                 125

Phe Pro Pro Lys Pro Lys Asp Thr Leu Ser Ile Ser Arg Thr Pro Glu
    130                 135                 140

Val Thr Cys Met Val Val Asp Leu Glu Asp Pro Glu Val Gln Ile Ser
```

```
145                 150                 155                 160

Trp Phe Val Asp Asn Gln Glu Val His Ala Ala Lys Thr Asn Ser Arg
                165                 170                 175

Glu Gln Gln Phe Asn Ser Thr Phe Arg Val Val Ser Val Leu Pro Ile
            180                 185                 190

Gln His Gln Asp Trp Leu Lys Gly Lys Val Phe Lys Cys Lys Val Asn
        195                 200                 205

Asn Lys Ala Leu Pro Ser Pro Ile Glu Arg Thr Ile Ser Lys Ala Arg
    210                 215                 220

Gly Glu Pro His Gln Pro Ser Val Tyr Val Leu Pro Pro Pro Arg Asp
225                 230                 235                 240

Glu Met Ser Arg Thr Thr Ile Ser Val Thr Cys Leu Val Lys Asp Phe
                245                 250                 255

Tyr Pro Pro Asp Ile Asp Val Glu Trp Gln Ser Asn Gly Arg Gln Leu
            260                 265                 270

Pro Glu Ala Ser Val Arg Thr Thr Pro Pro Gln Leu Asp Ala Asp Gly
        275                 280                 285

Ser Tyr Phe Leu Tyr Ser Lys Leu Ser Val Asp Lys Ala His Trp Gln
    290                 295                 300

Arg Gly Asp Thr Phe Thr Cys Ala Val Leu His Glu Ala Leu His Asn
305                 310                 315                 320

His His Thr Gln Lys Ser Ile Ser Gln Ser Pro Gly Lys
                325                 330


<210> SEQ ID NO 2
<211> LENGTH: 333
<212> TYPE: PRT
<213> ORGANISM: Artificial
<220> FEATURE:
<223> OTHER INFORMATION: Ferret derived heavy chain-Fc S252Y

<400> SEQUENCE: 2

Ala Ser Thr Thr Ala Pro Ser Val Phe Pro Leu Ala Pro Ser Cys Gly
1               5                   10                  15

Ala Thr Pro Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Asp Thr
65                  70                  75                  80

Phe Ile Cys Thr Val Ala His Pro Ala Ser Asn Thr Lys Val Asp Lys
                85                  90                  95

Arg Val Thr Gln Gly Gly Pro Pro His Thr Asp Pro Cys Lys Lys Cys
            100                 105                 110

Pro Gln Pro Pro Ala Cys Asp Met Leu Gly Gly Pro Ser Val Phe Met
        115                 120                 125

Phe Pro Pro Lys Pro Lys Asp Thr Leu Tyr Ile Ser Arg Thr Pro Glu
    130                 135                 140

Val Thr Cys Met Val Val Asp Leu Glu Asp Pro Glu Val Gln Ile Ser
145                 150                 155                 160

Trp Phe Val Asp Asn Gln Glu Val His Ala Ala Lys Thr Asn Ser Arg
                165                 170                 175

Glu Gln Gln Phe Asn Ser Thr Phe Arg Val Val Ser Val Leu Pro Ile
```

```
            180                 185                 190

Gln His Gln Asp Trp Leu Lys Gly Lys Val Phe Lys Cys Lys Val Asn
        195                 200                 205

Asn Lys Ala Leu Pro Ser Pro Ile Glu Arg Thr Ile Ser Lys Ala Arg
    210                 215                 220

Gly Glu Pro His Gln Pro Ser Val Tyr Val Leu Pro Pro Pro Arg Asp
225                 230                 235                 240

Glu Met Ser Arg Thr Thr Ile Ser Val Thr Cys Leu Val Lys Asp Phe
                245                 250                 255

Tyr Pro Pro Asp Ile Asp Val Glu Trp Gln Ser Asn Gly Arg Gln Leu
            260                 265                 270

Pro Glu Ala Ser Val Arg Thr Thr Pro Pro Gln Leu Asp Ala Asp Gly
        275                 280                 285

Ser Tyr Phe Leu Tyr Ser Lys Leu Ser Val Asp Lys Ala His Trp Gln
    290                 295                 300

Arg Gly Asp Thr Phe Thr Cys Ala Val Leu His Glu Ala Leu His Asn
305                 310                 315                 320

His His Thr Gln Lys Ser Ile Ser Gln Ser Pro Gly Lys
                325                 330


<210> SEQ ID NO 3
<211> LENGTH: 333
<212> TYPE: PRT
<213> ORGANISM: Artificial
<220> FEATURE:
<223> OTHER INFORMATION: Ferret derived Heavy Chain-Fc S252M

<400> SEQUENCE: 3

Ala Ser Thr Thr Ala Pro Ser Val Phe Pro Leu Ala Pro Ser Cys Gly
1               5                   10                  15

Ala Thr Pro Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Asp Thr
65                  70                  75                  80

Phe Ile Cys Thr Val Ala His Pro Ala Ser Asn Thr Lys Val Asp Lys
                85                  90                  95

Arg Val Thr Gln Gly Gly Pro Pro His Thr Asp Pro Cys Lys Lys Cys
            100                 105                 110

Pro Gln Pro Pro Ala Cys Asp Met Leu Gly Gly Pro Ser Val Phe Met
        115                 120                 125

Phe Pro Pro Lys Pro Lys Asp Thr Leu Met Ile Ser Arg Thr Pro Glu
    130                 135                 140

Val Thr Cys Met Val Val Asp Leu Glu Asp Pro Glu Val Gln Ile Ser
145                 150                 155                 160

Trp Phe Val Asp Asn Gln Glu Val His Ala Ala Lys Thr Asn Ser Arg
                165                 170                 175

Glu Gln Gln Phe Asn Ser Thr Phe Arg Val Val Ser Val Leu Pro Ile
            180                 185                 190

Gln His Gln Asp Trp Leu Lys Gly Lys Val Phe Lys Cys Lys Val Asn
        195                 200                 205

Asn Lys Ala Leu Pro Ser Pro Ile Glu Arg Thr Ile Ser Lys Ala Arg
```

```
    210                 215                 220

Gly Glu Pro His Gln Pro Ser Val Tyr Val Leu Pro Pro Pro Arg Asp
225                 230                 235                 240

Glu Met Ser Arg Thr Thr Ile Ser Val Thr Cys Leu Val Lys Asp Phe
                245                 250                 255

Tyr Pro Pro Asp Ile Asp Val Glu Trp Gln Ser Asn Gly Arg Gln Leu
            260                 265                 270

Pro Glu Ala Ser Val Arg Thr Thr Pro Pro Gln Leu Asp Ala Asp Gly
        275                 280                 285

Ser Tyr Phe Leu Tyr Ser Lys Leu Ser Val Asp Lys Ala His Trp Gln
    290                 295                 300

Arg Gly Asp Thr Phe Thr Cys Ala Val Leu His Glu Ala Leu His Asn
305                 310                 315                 320

His His Thr Gln Lys Ser Ile Ser Gln Ser Pro Gly Lys
                325                 330


<210> SEQ ID NO 4
<211> LENGTH: 333
<212> TYPE: PRT
<213> ORGANISM: Artificial
<220> FEATURE:
<223> OTHER INFORMATION: Ferret derived Heavy Chain-Fc YTE

<400> SEQUENCE: 4

Ala Ser Thr Thr Ala Pro Ser Val Phe Pro Leu Ala Pro Ser Cys Gly
1               5                   10                  15

Ala Thr Pro Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Asp Thr
65                  70                  75                  80

Phe Ile Cys Thr Val Ala His Pro Ala Ser Asn Thr Lys Val Asp Lys
                85                  90                  95

Arg Val Thr Gln Gly Gly Pro Pro His Thr Asp Pro Cys Lys Lys Cys
            100                 105                 110

Pro Gln Pro Pro Ala Cys Asp Met Leu Gly Gly Pro Ser Val Phe Met
        115                 120                 125

Phe Pro Pro Lys Pro Lys Asp Thr Leu Tyr Ile Thr Arg Glu Pro Glu
    130                 135                 140

Val Thr Cys Met Val Val Asp Leu Glu Asp Pro Glu Val Gln Ile Ser
145                 150                 155                 160

Trp Phe Val Asp Asn Gln Glu Val His Ala Ala Lys Thr Asn Ser Arg
                165                 170                 175

Glu Gln Gln Phe Asn Ser Thr Phe Arg Val Val Ser Val Leu Pro Ile
            180                 185                 190

Gln His Gln Asp Trp Leu Lys Gly Lys Val Phe Lys Cys Lys Val Asn
        195                 200                 205

Asn Lys Ala Leu Pro Ser Pro Ile Glu Arg Thr Ile Ser Lys Ala Arg
    210                 215                 220

Gly Glu Pro His Gln Pro Ser Val Tyr Val Leu Pro Pro Pro Arg Asp
225                 230                 235                 240

Glu Met Ser Arg Thr Thr Ile Ser Val Thr Cys Leu Val Lys Asp Phe
```

```
                245                 250                 255

Tyr Pro Pro Asp Ile Asp Val Glu Trp Gln Ser Asn Gly Arg Gln Leu
            260                 265                 270

Pro Glu Ala Ser Val Arg Thr Thr Pro Pro Gln Leu Asp Ala Asp Gly
        275                 280                 285

Ser Tyr Phe Leu Tyr Ser Lys Leu Ser Val Asp Lys Ala His Trp Gln
    290                 295                 300

Arg Gly Asp Thr Phe Thr Cys Ala Val Leu His Glu Ala Leu His Asn
305                 310                 315                 320

His His Thr Gln Lys Ser Ile Ser Gln Ser Pro Gly Lys
                325                 330


<210> SEQ ID NO 5
<211> LENGTH: 107
<212> TYPE: PRT
<213> ORGANISM: Mustela putorius furo

<400> SEQUENCE: 5

Asn Asp Ala Gln Pro Ser Val Phe Leu Phe Gln Pro Ser Pro Asp Gln
1               5                   10                  15

Leu His Thr Gly Ser Ala Ser Val Val Cys Met Leu Asn Gly Phe Tyr
            20                  25                  30

Pro Arg Glu Val Asn Val Lys Trp Lys Val Asp Gly Val Thr Lys Asn
        35                  40                  45

Thr Gly Ile Leu Glu Ser Val Thr Glu Gln Asp Ser Lys Asp Ser Thr
    50                  55                  60

Tyr Ser Leu Ser Ser Thr Leu Thr Met Pro Ser Thr Glu Tyr Leu Ser
65                  70                  75                  80

His Glu Lys Tyr Ser Cys Glu Val Thr His Lys Ser Leu Ser Ser Pro
        85                  90                  95

Leu Val Lys Ser Phe Gln Arg Ser Glu Cys Gln
    100                 105


<210> SEQ ID NO 6
<211> LENGTH: 1002
<212> TYPE: DNA
<213> ORGANISM: Mustela putorius furo

<400> SEQUENCE: 6

gcttccacca cggccccatc ggttttccca ctggccccca gctgcggggc cacccccgga     60

tccacagtgg ccctggcctg cctggtgtcc ggctacttcc ctgagcctgt cactgtgtcc    120

tggaactccg gctccttgac cagcggtgtg cacaccttcc cgtctgtcct gcagtcctcg    180

ggcctctact ctctcagcag catggtgacc gtgccctcca gcaggtggcc cagcgacacc    240

ttcatctgca ccgtggccca cccagccagt aacaccaagg tggacaagag agtgacccaa    300

ggaggacctc ctcacactga cccatgcaaa aaatgtcccc aacctccagc atgtgatatg    360

ctcggaggac cttcagtctt catgttcccc ccgaaaccca aggacaccct ctccatttcc    420

cgaacccccg aggttacatg catggtggtg gacctggaag accctgaggt ccagatcagc    480

tggtttgtgg acaaccagga ggtgcacgcg gccaagacga attcgcgtga gcagcagttc    540

aacagcacct tccgtgtggt cagtgtcctc cccatccagc accaggactg gctcaagggg    600

aaggtcttca agtgcaaggt caacaacaaa gctctcccat cccccattga gaggaccatc    660

tccaaggcca gaggggaacc ccatcagccc agtgtgtatg tcctgccccc accccgggac    720

gagatgagca ggaccaccat cagtgtgacc tgcctggtca aagacttcta cccacctgac    780
```

```
atcgatgtgg agtggcagag caacggccgt cagttaccag aggccagtgt ccgaacaacc    840

ccgccccagc tggatgcgga cggcagctac ttcctctaca gcaagctctc cgtggacaag    900

gcgcactggc agcggggaga caccttcacg tgtgcggtgc tgcatgaagc cctacacaac    960

catcacacgc agaagtccat ctcccagtct ccgggtaaat ga                      1002
```

<210> SEQ ID NO 7
<211> LENGTH: 324
<212> TYPE: DNA
<213> ORGANISM: Mustela putorius furo

<400> SEQUENCE: 7

```
aatgatgccc agccatccgt ctttctgttc caaccatctc cggaccagtt acataccggc     60

agtgcctctg tcgtgtgcat gctgaatggc ttctacccca gagaagtcaa tgtcaaatgg    120

aaggttgatg gtgttaccaa aaacacaggc atcctggaaa gtgtcacaga acaagacagc    180

aaggacagca cctacagcct cagcagcacc ttgacgatgc ccagtacgga gtacctaagt    240

catgagaagt actcctgtga ggtcactcac aagagcctgt cctcccctct tgtcaagagc    300

ttccaaagga gcgagtgcca atga                                           324
```

<210> SEQ ID NO 8
<211> LENGTH: 296
<212> TYPE: PRT
<213> ORGANISM: Mustela putorius furo

<400> SEQUENCE: 8

```
Met Gly Val Pro Arg Pro Arg Ser Trp Gly Leu Gly Phe Leu Leu Phe
1               5                   10                  15

Leu Leu Pro Thr Val Arg Ala Glu Ser Asn Leu Ser Leu Leu Tyr His
            20                  25                  30

Leu Thr Ala Val Ser Ser Pro Ala Pro Gly Ala Pro Ala Phe Trp Val
        35                  40                  45

Ser Gly Trp Leu Gly Pro Gln Gln Tyr Leu Ser Tyr Asn Asn Leu Arg
    50                  55                  60

Ala Glu Ala Glu Pro Cys Gly Ala Trp Val Trp Glu Asn Gln Val Ser
65                  70                  75                  80

Trp Tyr Trp Glu Lys Glu Thr Thr Asp Leu Arg Ser Lys Gln Glu Leu
                85                  90                  95

Phe Leu Glu Gly Leu Lys Ala Leu Gly Lys Gly Gly Pro Tyr Thr Leu
            100                 105                 110

Gln Gly Leu Leu Gly Cys Glu Leu Gly Pro Asp Asn Ala Ser Val Pro
        115                 120                 125

Val Ala Lys Phe Ala Leu Asn Gly Glu Asp Phe Met Thr Phe Asp Pro
    130                 135                 140

Lys Leu Gly Thr Trp Asp Gly Asp Trp Pro Glu Thr Glu Thr Ile Gln
145                 150                 155                 160

Lys Thr Trp Met Gln His Ala Gly Ala Val Ser Lys Glu Arg Thr Phe
                165                 170                 175

Leu Leu Asn Ser Cys Pro Gln Arg Leu Leu Gly His Leu Glu Arg Gly
            180                 185                 190

Arg Gly Asn Leu Glu Trp Lys Glu Pro Pro Ser Met Arg Leu Lys Ala
        195                 200                 205

Arg Pro Gly Ser Pro Gly Phe Ser Val Leu Thr Cys Ser Ala Phe Ser
    210                 215                 220
```

-continued

Phe Tyr Pro Pro Glu Leu Gln Leu Arg Phe Leu Arg Asn Gly Leu Ala
225 230 235 240

Val Gly Ser Gly Glu Gly Asp Phe Gly Pro Asn Gly Asp Gly Ser Phe
245 250 255

His Ala Trp Ser Ser Leu Thr Val Lys Ser Gly Asp Glu His His Tyr
260 265 270

Arg Cys Val Val Gln His Ala Gly Leu Pro Gln Pro Leu Thr Val Glu
275 280 285

Leu Glu Ser Pro Ala Arg Ser Ser
290 295

<210> SEQ ID NO 9
<211> LENGTH: 330
<212> TYPE: PRT
<213> ORGANISM: Mustela vision

<400> SEQUENCE: 9

Ala Ser Thr Thr Ala Pro Ser Val Phe Pro Leu Ala Pro Ser Cys Gly
1 5 10 15

Ala Thr Pro Gly Pro Thr Val Ala Leu Ala Cys Leu Val Ser Gly Tyr
20 25 30

Phe Pro Glu Pro Val Thr Val Ser Trp Asn Ser Gly Ser Leu Thr Ser
35 40 45

Gly Val His Thr Phe Pro Ser Val Leu Gln Ser Ser Gly Leu Tyr Ser
50 55 60

Leu Ser Ser Met Val Thr Val Pro Ser Ser Arg Trp Pro Ser Asp Thr
65 70 75 80

Phe Ile Cys Thr Val Ala His Pro Ala Ser Asn Thr Arg Val Asp Lys
85 90 95

Arg Val Pro Pro Gly Lys Ile Pro Pro Pro Cys Thr Cys Pro Pro Arg
100 105 110

Ala Glu Cys Asp Met Leu Gly Gly Pro Ser Val Phe Met Phe Pro Pro
115 120 125

Lys Pro Arg Asp Thr Leu Ser Ile Ser Arg Thr Pro Glu Val Thr Cys
130 135 140

Met Val Val Asp Leu Glu Asp Pro Glu Val Gln Ile Ser Trp Phe Val
145 150 155 160

Asp Asn Gln Glu Met His Thr Ala Lys Thr Asn Ser Arg Glu Gln Gln
165 170 175

Phe Asn Ser Thr Phe Arg Val Val Ser Val Leu Pro Ile Gln His Gln
180 185 190

Asp Trp Leu Lys Gly Lys Val Phe Lys Cys Lys Val Asn Asn Lys Ala
195 200 205

Leu Pro Ser Pro Ile Glu Arg Thr Ile Ser Lys Val Lys Gly Glu Ala
210 215 220

His Gln Pro Ser Val Tyr Val Leu Pro Pro Ser Arg Asp Glu Leu Ser
225 230 235 240

Lys Asn Arg Val Ser Val Thr Cys Met Val Lys Asp Phe Tyr Pro Pro
245 250 255

Asp Ile Asp Val Glu Trp Gln Ser Asn Gly Gln Gln Phe Pro Glu Ala
260 265 270

Ser Val Arg Thr Thr Pro Pro Gln Leu Asp Ala Asp Gly Thr Tyr Phe
275 280 285

Leu Tyr Ser Lys Leu Ser Val Asp Lys Ala Arg Trp Gln Gly Gly Glu
290 295 300

-continued

```
Thr Phe Thr Cys Ala Val Leu His Glu Ala Leu His Asn His His Thr
305                 310                 315                 320

Gln Lys Ser Ile Ser Gln Ser Pro Gly Lys
                325                 330


<210> SEQ ID NO 10
<211> LENGTH: 107
<212> TYPE: PRT
<213> ORGANISM: Mustela vision

<400> SEQUENCE: 10

Asn Asp Ala Gln Pro Ser Val Phe Leu Phe Gln Pro Ser Gln Asp Gln
1               5                   10                  15

Leu His Thr Gly Ser Ala Ser Val Val Cys Leu Leu Asn Gly Phe Tyr
            20                  25                  30

Pro Lys Glu Val Thr Val Lys Trp Met Val Asp Gly Val Thr Lys Asn
        35                  40                  45

Thr Gly Ile Leu Glu Ser Val Thr Glu Gln Asp Ser Lys Asp Ser Thr
    50                  55                  60

Tyr Ser Leu Ser Ser Thr Leu Thr Ile Pro Ser Thr Glu Tyr Leu Ser
65                  70                  75                  80

His Glu Thr Tyr Ser Cys Glu Val Thr His Lys Ser Leu Ser Ser Pro
                85                  90                  95

Leu Val Lys Ser Phe Gln Arg Ser Glu Cys Gln
            100                 105
```

ANTIBODIES WITH IMPROVED HALF-LIFE IN FERRETS

CROSS-REFERENCE TO RELATED APPLICATIONS

This application claims the benefit of U.S. Provisional Application Ser. No. 61/953,149, filed 14 Mar. 2014. The entire contents of the aforementioned application are incorporated herein by reference in their entirety.

FIELD OF THE INVENTION

The present invention relates to antibodies, immunoglobulin constructs, or immunoglobulin fusion proteins whose in vivo half-life is increased in ferrets by a modified ferret IgG Fc region.

BACKGROUND OF THE INVENTION

Ferrets are susceptible to infection with human influenza virus and show symptoms that mimic those seen in humans making them a useful laboratory model (Maher J. *Lab Animal* 2004; 33(9): 50-53; Van der Laan J, Herberts R, Lanbkin-Williams R, Boyers A, Mann A, Oxford J. *Expert Rev Vaccines* 2008; 7(6): 783-793). For this reason, ferrets have routinely been used to study the effects of influenza vaccines. A more recent application has been the study of human monoclonal antibodies directed against influenza viruses in ferrets (Friesen R, Koudstaal W, Koldijk M, et al *PLOS One* 2010; 5(2): e9106). However, this and another study involving ferrets exposed to the Nipah virus (Bossart K, Zhu Z, Middleton D, et al. *PLOS Pathog* 2009; 5(10): e1000642) suggested that ferrets have an antibody clearance rate much faster than other commonly-used model species such as mice, rats and cynomolgus monkeys (Petkova S, Akilesh S, Sproule T J, et al. *Int. Immunol.* 2006; 18 (12): 1759-1769; Lin S Y, Cindy Nguyen C, Mendoza J L, et al. *JPET* 1999; 288 (1): 371-378).

This illustrates the critical limitations of the ferret model for use in the testing of monoclonal antibody therapeutics. The short half-life of human antibody therapeutics in the ferret necessitates high dosing frequency, increasing material requirements, thereby demanding greater resources. Moreover, a misunderstanding of the PK-PD relationship for fast-clearing antibodies may lead to misinterpretation of efficacy results. Thus, there is a need in the art to develop novel IgG variants with reduced immunogenicity and longer circulating half-life in ferrets. The present application meets these and other needs.

SUMMARY OF THE INVENTION

The present invention relates to molecules, in particular antibodies, immunoglobulin constructs, or immunoglobulin fusion proteins whose in vivo half-life is increased in a ferret by a modification of the ferret IgG Fc region. Specifically, these molecules have amino acid modifications, such as mutations, that increase the affinity of the ferret Fc for the ferret FcRn and hence the circulating half-life in a ferret.

The invention is based on discovery that the Fc modifications increase the circulating half-life of the molecule in ferrets relative to its unmodified counterpart. The advantages of increasing half-life of a molecule in a ferret will be immediately evident to the person skilled in the art. Such benefits include lower dosing and/or frequency of administration which preserve the ability to study the risk of adverse events in a ferret and reduces costs. Accordingly, such antibodies with increased half-life are of significant importance for pharmaceutical research.

Accordingly, in one embodiment, the present invention provides an isolated antibody, immunoglobulin construct, or immunoglobulin fusion protein comprising a ferret IgG Fc region modified relative to a corresponding unmodified ferret IgG Fc region wherein the ferret IgG Fc region comprises a substitution at amino acid residue 252 numbered according to the EU index as in Kabat, wherein the in vivo half-life of the modified antibody, immunoglobulin construct, or immunoglobulin fusion protein is increased in a ferret compared with the corresponding unmodified antibody, immunoglobulin construct or immunoglobulin fusion protein.

The increased in vivo half-life of the antibody, immunoglobulin construct or immunoglobulin fusion protein is determined by reference to the half-life of a corresponding antibody, immunoglobulin construct or immunoglobulin fusion protein which lacks the above substitution.

In one embodiment, the isolated antibody, immunoglobulin construct, or immunoglobulin fusion protein comprise substitutions S252Y or S252M numbered according to the EU index as in Kabat.

In a particular example, the antibody, immunoglobulin construct or immunoglobulin fusion protein comprises substitutions at each of residues 252, 254 and 256 of the ferret Fc region sequence numbered according to the EU index as in Kabat.

In a particular example, residue 252 is substituted with tyrosine (S252Y), residue 254 is substituted with threonine (S254T) and residue 256 is substituted with glutamic acid (T256E). These substitutions are referred to collectively as the "YTE modification."

The antibody according to the invention may be a chimeric antibody, ferret antibody, ferretized antibody, or a ferret veneered antibody.

In one example, the present invention provides an isolated antibody comprising:

a. a human or humanized Fab, and b. a ferret IgG Fc region modified relative to a corresponding unmodified ferret IgG Fc region wherein the ferret IgG Fc region comprises a substitution at amino acid residue 252 numbered according to the EU index as in Kabat;

wherein the in vivo half-life of the modified antibody is increased in a ferret compared with the corresponding unmodified antibody.

In one embodiment, the antibody comprises substitutions S252Y or S252M numbered according to the EU index as in Kabat.

In another embodiment, the antibody further comprises substitution S254T and T256E numbered according to the EU index as in Kabat.

In another example, the invention provides an isolated immunoglobulin construct comprising:

a. an antibody fragment; and b. a ferret lgG Fc region modified relative to a corresponding unmodified ferret lgG Fc region wherein the ferret IgG Fc region comprises a substitution at amino acid residue 252 numbered according to the EU index as in Kabat;

wherein the in vivo half-life of the modified immunoglobulin construct is increased in a ferret compared with the corresponding unmodified immunoglobulin construct.

In one embodiment, the isolated immunoglobulin construct comprises a ferret IgG Fc region.

Preferably, the isolated immunoglobulin construct comprises substitution S252Y or S252M according to the EU index as in Kabat.

In another embodiment, the isolated immunoglobulin construct further comprises substitutions S254T and T256E according to the EU index as in Kabat.

Specific antibody fragments include, but are not limited to (i) a Fab fragment (ii) an Fd fragment, (iii) an Fv fragment, (iv) a dAb fragment, (v) isolated CDR regions, (vi) F(ab')2 fragments, (vii) single chain Fv molecules, (scFv), (viii) bispecific single chain Fv, (ix) diabody, (x) triabody, and (xi) tetrabody.

The invention also provides an immunoglobulin fusion protein with increased in vivo half-life comprising a bioactive molecule recombinantly fused or chemically conjugated or engineered to contain a ferret IgG Fc region modified relative to a corresponding unmodified ferret IgG Fc region wherein the ferret IgG Fc region comprises a substitution at amino acid residue 252 numbered according to the EU index as in Kabat.

The bioactive molecule may include protein or non-protein agents or non-immunoglobulin proteins.

Preferably, the isolated immunoglobulin fusion protein comprises substitution S252Y or S252M numbered according to the EU index as in Kabat.

In another embodiment, the isolated immunoglobulin fusion protein further comprises substitutions S254T and T256E according to the EU index as in Kabat.

In another embodiment, the antibody or immunoglobulin construct according to the invention may be further recombinantly fused, chemically conjugated or engineered to contain to a moiety. The moiety according to the invention may be selected from, but not limited to a therapeutic agent which is directly or indirectly bound to the antibody, a cytotoxin, a radioisotope, an immunomodulatory agent, an anti-angiogenic agent, an anti-neovascularization and/or other vascularization agent, a toxin, an anti-proliferative agent, a pro-apoptotic agent, a chemotherapeutic agent and a therapeutic nucleic acid.

In one example, the antibody modified according to the present invention is an antibody that specifically binds to Respiratory Syncytial Virus F glycoprotein.

Accordingly, in one example, the present invention also provides an isolated antibody that specifically binds to Respiratory Syncytial Virus F glycoprotein comprising a ferret IgG Fc region modified relative to a corresponding unmodified ferret IgG Fc region comprising amino acid substitution S252Y or S252M numbered according to the EU index as in Kabat, and wherein the in vivo half-life of the modified antibody is increased in a ferret compared with the half-life of the corresponding unmodified antibody.

In another example the isolated antibody that specifically binds to Respiratory Syncytial Virus F glycoprotein further comprises substitutions S254T and T256E according to the EU index as in Kabat.

In another example, the present invention provides an antibody that specifically binds to Respiratory Syncytial Virus F glycoprotein, the antibody comprising a constant heavy chain sequence set forth in SEQ ID NOs: 1-4. In another example, the antibody that specifically binds to Respiratory Syncytial Virus F glycoprotein, further comprises a light chain comprising the variable and constant region sequences set forth in SEQ ID NO: 5.

The present invention also provides a method for increasing the in vivo half-life of an antibody or immunoglobulin construct in a ferret comprising a ferret IgG Fc region, the method comprising introducing amino acid substitutions S252Y or S252M numbered according to the EU index as in Kabat into the ferret Fc region sequence.

In another embodiment, the method for increasing the in vivo half-life of an antibody or immunoglobulin further comprises introducing amino acid substitutions S254T and T256E according to the EU index as in Kabat.

In a particular example, the above method can be used to increase the half-life of an anti-Respiratory Syncytial Virus F glycoprotein in a ferret.

The present invention also provides a method for increasing the in vivo half-life of an immunoglobulin fusion protein in a ferret comprising a ferret IgG Fc region, the method comprising introducing amino acid substitutions S252Y or S252M numbered according to the EU index as in Kabat into the ferret Fc region sequence.

In one embodiment, the method for increasing the in vivo half-life of an immunoglobulin fusion protein further comprises introducing amino acid substitutions S254T and T256E according to the EU index as in Kabat.

The invention also provides a method for increasing the in vivo half-life of a protein in a ferret by engineering it as a fusion protein comprising one of SEQ ID NOs: 1-4.

The invention also provides a fusion protein comprising one of SEQ ID NOs: 1-4.

The present invention also provides a nucleic acid encoding an antibody, immunoglobulin construct or immunoglobulin fusion protein as described herein according to any embodiment.

The present invention also provides a transformed cell expressing an antibody, immunoglobulin construct or immunoglobulin fusion protein as described herein according to any embodiment.

The present invention also provides a transformed cell comprising a nucleic acid encoding an antibody, immunoglobulin construct or immunoglobulin fusion protein as described herein.

BRIEF DESCRIPTION OF THE FIGURES

FIG. 3. Alignment of cloned ferret IgG heavy (SEQ ID NO:1) and light chain (SEQ ID NO:5) sequences with the previously reported partial ferret IgG sequence (portions of SEQ ID NOS:1 and 5) and mink sequences (SEQ ID NOS:9 and 10). The six amino acids derived from a primer based on the mink sequence are in light blue and a box denotes the putative hinge region.

FIGS. 6A-6D. First dose PK. mAb concentrations in the plasma from individual ferrets given the WT chimeric mAb (FIG. 6A) and the three variants (FIGS. 6B-6D) are shown.

Figure 1A:
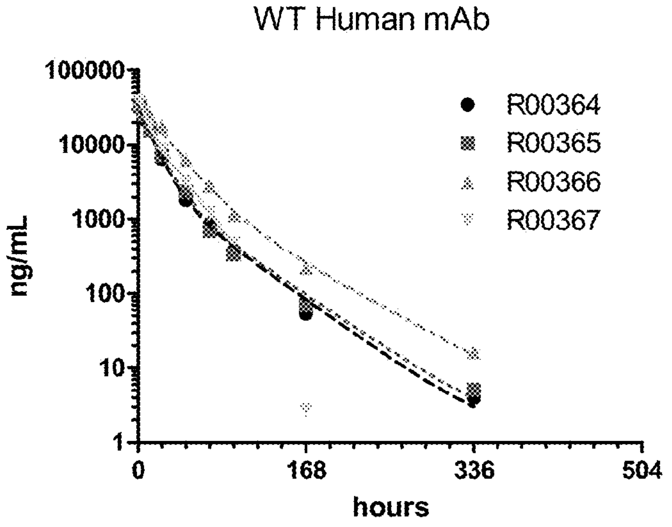
FIGS. 1A and 1B. Human mAb plasma concentrations over time. mAb concentrations in the plasma of individual ferrets (identified by R numbers) dosed with WT human mAb (FIG. 1A) or an LS mutant (FIG. 1B) are shown. Terminal half-life values are given a table below each graph. Outliers are circled.

Terminal half-life values based on a non-linear fit of the data points are given in the table below each graph.

FIGS. 7A-7D. Second dose PK. mAb concentrations in the plasma from individual ferrets given the WT chimeric mAb (FIG. 7A) and the three Fc (FIGS. 7B-7D) are shown. Terminal half-life values based on a non-linear fit of the data points are given in the table below each graph.

DETAILED DESCRIPTION OF THE INVENTION

General

The term "and/or," e.g., "X and/or Y" shall be understood to mean either "X and Y" or "X or Y" and shall be taken to provide explicit support for both meanings or for either meaning.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a," "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the disclosure is to be applied mutatis mutandis to each and every other embodiment unless specifically stated otherwise.

Those skilled in the art will appreciate that the disclosure herein is susceptible to variations and modifications other than those specifically described. It is to be understood that the disclosure encompasses all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

The compositions of matter and methods described herein are produced or performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). *Biochem. Biophys. Res. Commun.* 73 336-342; Merrifield, R. B. (1963). *J. Am. Chem. Soc.* 85, 2149-2154; Barany, G. and Merrifield, R. B. (1979) in The Peptides (Gross, E. and Meienhofer, J. eds.), vol. 2, pp. 1-284, Academic Press, New York. 12. Wunsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. *J. Peptide Protein Res.* 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000), ISBN 0199637970, whole of text.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

DEFINITIONS

As used herein the term "corresponding" unmodified antibody means an antibody of the same sequence as the modified antibody but without the changes to the amino acid sequence described herein, in particular the Fc region.

The term "epitope" is intended to refer to the part of an antigenic molecule to which an antibody is produced and to which the antibody will bind. The term "epitope," as used herein, refers to (a) portion(s) of a peptide having antigenic or immunogenic activity in an animal, preferably a vertebrate, more preferably a mammal, and most preferably in a human or a ferret. Epitopes may comprise proteins, protein fragments, peptides, carbohydrates, lipids, and other molecules, but for the purposes of the present invention are most commonly short oligopeptides. The term "epitope" is intended to encompass an "immunogenic epitope," an "antigenic epitope," or "antigen epitope."

The term "antibody" as used herein refers to a molecule that is capable of binding to a target through at least one epitope recognition site, located in the variable region of the immunoglobulin molecule. The terms immunoglobulin and antibody may be used interchangeably throughout the specification. The immunoglobulin or antibody molecule includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, Superhumanized® antibodies, half antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50-70 kD) covalently linked and two light chains (~23 kD each). Each heavy and light chain comprises variable regions and constant domains. A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ϵ, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are 110 amino acids in length) and one or more constant domains at the C-terminus. The constant domain of the light chain ($C_L$ which is ~110 amino acids in length) is aligned with and disulfide bonded to the first constant domain of the heavy chain ($C_H1$ which is 330-440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Unmodified antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass.

The term "immunoglobulin construct" as used herein refers to a construct comprising at least a constant region from a ferret antibody. Preferably, the term is intended to refer to a construct comprising at least light and heavy chain constant domains and hinge region from a ferret antibody.

The term "constant region" or "constant fragment" refers to the portion of an immunoglobulin or antibody molecule having a core conserved amino acid sequence relative to the other portion of the immunoglobulin or antibody, termed the variable region, which contains the antigen binding site. In the heavy chain, the constant region contains the CH1, CH2 and CH3 domains.

The term "Fc region" as used herein refers to the portion of an antibody or immunoglobulin molecule that correlates to a crystallizable fragment obtained by papain digestion of an IgG molecule. The Fc region consists of the C-terminal region of an IgG heavy chain-made up of the C-terminal approximately half of the two heavy chains of an IgG molecule that are linked by disulfide bonds. Although boundaries may vary slightly (in some cases it includes part of the hinge), as numbered according to the EU index of Kabat, the Fc region extends from amino acid 231 to amino acid 447. The Fc region of an IgG comprises two constant domains, CH2 and CH3. The CH2 domain of a human IgG Fc region usually extends from amino acid 231 to amino acid 341 according to the EU index of Kabat. The CH3 domain of a human IgG Fc region usually extends from amino acids 342 to 447 according to the EU index of Kabat. The Fc region has no antigen binding activity but contains the carbohydrate moiety and the binding site for the Fc receptor, including the neonatal Fc receptor (FcRn).

Throughout the specification, the numbering of residues in an immunoglobulin heavy chain is that of the EU index or numbering system of Kabat (Kabat et al., Sequences of Proteins of Immunological Interest $5^{th}$ Ed., Washington D.C. United States Department of Health and Human Services, 1991, National Institutes of Health, Bethesda. The "EU index as Kabat" refers to the numbering of the human IgG1 EU antibody (Edelman et al., *Proc. Natl. Acad. USA,* 63, 78-85, 1969). The amino acid sequences of IgG2, IgG3 and IgG4 isotypes are aligned with the IgG1 sequence by placing the first and last cysteine residues of the respective hinge regions, which form the inter-heavy chain S—S bonds, in the same positions. The numbering in the ferret sequence is based on homology alignment with the human Fc sequence. Amino acid residues 252, 254 and 256 according to the EU index as in Kabat is located within the immunoglobulin heavy chain CH2 domain of the Fc region. These residues have been implicated in binding of the Fc region to the FcRn and hence are implicated in altering antibody half-life in other species.

The term "FcRn" as used herein refers to an Fc receptor ("n" indicating neonatal) which is involved in transfer of maternal IgGs to a mammalian fetus through the mammalian placenta to a neonate from the colostrum through the small intestine. The FcRn is also involved in the maintenance of constant serum IgG levels by binding the IgG molecules and recycling them into the serum. The binding of FcRn to IgG molecules is strictly pH dependent with optimum binding at pH 6.0. The FcRn is typically complexed with beta2 microglobulin.

The "hinge region" as used herein refers to a proline-rich portion of an immunoglobulin heavy chain between the Fc and Fab regions that confers mobility on the two Fab arms of the antibody molecule. It is located between the first and second constant domains of the heavy chain. The hinge region includes cysteine residues which are involved in inter-heavy chain disulfide bonds. It is generally defined as stretching from Glu216 to Pro230 of human IgG1 according to the EU numbering system of Kabat (or Glu226 to Pro243 according to the numbering system of Kabat). Hinge regions of other IgG isotypes may be aligned with the IgG1 sequence by placing the first and last cysteine residues forming inter-heavy chain disulphide (S—S) bonds in the same positions (see for example WO 2010/080538). The hinge region includes cysteine residues which are involved in inter-heavy chain disulfide bonds.

The term "Fab" as used herein is intended to refer to a region of an antibody composed of one constant and one variable domain of each of the heavy and the light chains (monovalent antigen-binding fragment), but wherein the heavy chain is truncated such that it lacks the CH2 and CH3 domain (ie VH, CH1, VL, and CL), and may also lack some or all of the hinge region. It can be produced by digestion of a whole antibody with the enzyme papain. Fab may refer to this region in isolation, or this region in the context of a full length antibody, immunoglobulin construct or Fab fusion protein.

By "scFv" it is meant an antibody fragment comprising the VH and VL domains of an antibody, wherein these domains are present in a single polypeptide chain. See, for example, U.S. Pat. Nos. 4,946,778, 5,260,203, 5,455,030, and 5,856,456. Generally, the Fv polypeptide further comprises a polypeptide linker between the $V_H$ and VL domains that enables the scFv to form the desired structure for antigen-binding. For a review of scFv see Pluckthun (1994) The Pharmacology of Monoclonal Antibodies vol 1 13 ed. Rosenburg and Moore (Springer-Verlag, New York) pp 269-315. The VH and VL domain complex of Fv fragments may also be stabilized by a disulfide bond (U.S. Pat. No. 5,747,654).

The term "isolated" as used herein refers to a biomolecule (protein or nucleic acid) removed from its native environment. Preferably, the biomolecule is substantially purified.

By "substantially purified" is meant that the biomolecule is substantially free of cellular material or other contaminating proteins from the cell or tissue source from which it is derived, or is substantially free from chemical precursors or other chemicals when chemically synthesized. The language includes preparations which are separated from cellular components of the cells from which it is isolated or recombinantly produced.

The term "immunoglobulin fusion protein" refers to a bioactive molecule which is linked or attached to a modified ferret lgG Fc region. Fusion proteins are discussed in further detail later.

The term "in vivo half-life" as used herein refers to a circulating half-life of a particular antibody, containing an Fc region in the circulation of a given animal and is represented by a time required for half the quantity administered in the animal to be cleared from the circulation. When a clearance curve of a given antibody, according to the invention is constructed as a function of time the curve is usually biphasic with a rapid alpha phase which represents an equilibration of the injected IgG molecules between the intra and extra vascular space and which is, in part determined by the size of the molecules, and a longer beta phase which represents the catabolism of the IgG molecules in the intravascular space. The term "in vivo half-life" practically corresponds to the half-life of the modified or unmodified immunoglobulin in the beta phase.

The term "increased half-life" as used herein means that the antibody modified according to the invention has a greater persistence in the serum or plasma and/or takes a greater period of time to reduce to half the maximal measured serum or plasma concentration relative to the same antibody that does not contain the same substitutions.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody variable region. Similarly, if a nucleic acid encoding the protein is isolated and expressed using recombinant means, the resulting protein is a recombinant protein comprising an antibody antigen binding domain. A term recombinant also encompasses an antibody expressed by artificial recombinant means when it is within a cell, tissue or subject, e.g., in which it is expressed.

The term "specifically binds" refers to a molecule (eg. antibody, immunoglobulin construct or immunoglobulin lgG4 fusion protein) that specifically or preferentially binds to an antigen (e.g., eptiope or immune complex) and does not specifically bind to (i.e. cross-react with) antigens, such as, for example, other structurally or functionally related proteins, or proteins with sequence homology. A molecule that specifically binds to an antigen may bind to other peptides or polypeptides with lower affinity as determined by, e.g., immunoassays, BIAcore, or other assays known in the art. Preferably, molecules that specifically bind an antigen do not cross-react with other proteins. Molecules that specifically bind an antigen can be identified, for example, by immunoassays, BIAcore, or other techniques known to those of skill in the art. By way of non-limiting example, an antibody may be considered to bind to an antigen preferentially if it binds said antigen with dissociation constant ($K_D$) that is less than the antibody's $K_D$ for another antigen. In another non-limiting example, an antibody may be considered to bind a first antigen preferentially if it binds said first antigen with an affinity that is at least one order of magnitude less than the antibody's $K_D$ for the second antigen. In another non-limiting embodiment, an antibody may be considered to bind a first antigen preferentially if it binds said first antigen with an affinity that is at least two orders of magnitude less than the antibody's $K_D$ for the second antigen.

Amino Acid Substitutions

Methods of substituting amino acids are known in the art. For example, amino acid substitutions can be made by site-directed mutagenesis (for example, Zoller and Smith *Nucl. Acids Res.* 10:6487 (1982)). Mutagenesis can be performed by synthesizing an oligonucleotide having one or more modifications within the sequence of the constant domain of an antibody to be modified. Site-specific mutagenesis allows the production of mutants through the use of specific oligonucleotide sequences which encode the DNA sequence of the desired mutation, as well as a sufficient number of adjacent oligonucleotides to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generate a library of mutants. The technique of site-specific mutagenesis is well known in the art, (see, e.g., Kunkel et al., *Methods Enzymol.,* 154:367-82, 1987). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage. Site directed mutagenesis has also been used to identify amino acid residues that influence plasma clearance of murine IgG1 hinge-Fc fragments as described in Kim Jin-Kyoo et al., (1994) Eur. J. Immunol. 24:542-548). Alternatively, the use of PCR with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.,* 18(6):1656, 1987, and Upender et al., *Biotechniques,* 18(1):29-30, 32, 1995, for PCR-mediated mutagenesis procedures. PCR employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques,* 16(3):410-2, 1994).

Other methods known to those of skill in art of producing sequence variants of the Fc region of an antibody or an FcRn binding domain thereof can be used. For example, recombinant vectors encoding the amino acid sequence of the constant domain of an antibody or a fragment thereof may be treated with mutagenic agents, such as hydroxylamine, to obtain sequence variants.

Mutants that result in increased affinity for FcRn and increased in vivo half-life can be screened using routine assays such as those described later. Exemplary amino acid substitutions include S252M, S252Y, or S252Y S254T, and T256E according to the EU Kabat numbering system.

Antibodies of the Invention

The antibodies according to the invention includes any immunoglobulin molecule or antibody that binds, (as determined by immunoassays known in the art for assaying specific antigen-antibody binding) an antigen and contains an Fc region. The antibodies may be polyclonal, monoclonal or monospecific, bi-specific (in the context of multimeric forms of the antibody), chimeric, or ferretized. In another example, the antibodies of the present invention may be monospecific, (or bispecific, trispecific or of greater multi-specificity if present in multimeric form). In particular, the antibody is a monospecific tetramer.

The antibody may be from any mustelid origin. Preferably, the antibody is from ferret or ferret/human chimerized. As used herein the term "human" antibody includes antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598.

Ferret Antibody Derivatives

The present invention also provides antibodies that comprise, or alternatively consist of, variants (including derivatives) of the antibody molecules (e.g. the $V_H$ domains and/or $V_L$ domains) described herein, which antibodies specifically bind antigen peptides (for example, the Respiratory Syncytial Virus F glycoprotein). Standard techniques known to those of skill in the art can be used to introduce mutations in the nucleotide sequence encoding a molecule of the invention, including for example, site-directed mutagenesis and PCR-mediated mutagenesis which result in amino acid substitutions.

Antibody derivatives according to the invention also encompass conservative amino acid substitutions into the immunoglobulin $V_L$ and/or $V_H$ region. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind antigen peptides of the invention (e.g. the ability to bind antigen peptides of the invention).

The term "conservative substitution" shall be taken to mean amino acid substitutions set forth in Table 1.

TABLE 1

Exemplary Substitutions

| Original residue | Exemplary substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro; ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

For example, it is possible to introduce mutations only in framework regions or only in CDR regions of an antibody molecule. Introduced mutations may be silent or neutral missense mutations, i.e. have no, or little, effect on the antibody's ability to bind antigen. These types of mutations may be useful to optimize codon usage, or improve antibody production from a cell line.

Alternatively, non-neutral missense mutations may alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to specifically bind antigen peptides of the invention) can be determined using techniques described herein or by routinely modifying techniques known in the art.

The antibodies of the invention include derivatives that are otherwise modified by covalent attachment of any type of molecule to the antibody such that covalent attachment does not prevent the antibody from binding antigen. For example, the antibody derivatives include antibodies that have been modified, for example, by glycosylation, acetylation, pegylation, phosphorylation, amidation, derivatisation by known protecting/blocking groups, proteolytic cleavage, linkage to a cellular ligand or other protein etc. Any of numerous chemical modifications may be carried out by techniques known in the art, including specific chemical cleavage, acetylation, formylation, metabolic synthesis of tunicamycin etc. Additionally, the derivative may contain one or more non-classical amino acids.

In addition, antibodies of the invention may be chemically synthesized. For example, a peptide corresponding to a portion of a protein can by synthesized by use of a peptide synthesizer. Furthermore, if desired, non-classical amino acids or chemical amino acid analogs can be introduced as substitutions and/or additional into the sequence of one, any, both, several or all of the polypeptides of the complex.

Non-classical amino acids include, but are not limited to, the D-isomers of the common amino acids, fluoro-amino acids, designer amino acids such as beta-methyl amino acids, C gamma-methyl amino acids, N gamma-methyl amino acids, and, and amino acid analogs in general.

The present invention also provides immunoconjugates comprising an antibody or immunoglobulin contract of the present invention conjugated to a distinct moiety. Examples of distinct moieties include, but are not limited to, a cytotoxin, a radioisotope (e.g., iodine-131, yttrium-90 or indium-111), an immunomodulatory agent, an anti-angiogenic agent, an anti-neovascularization and/or other vascularization agent, a toxin, an anti-proliferative agent, a pro-apoptotic agent, a chemotherapeutic agent and a therapeutic nucleic acid.

A cytotoxin includes any agent that is detrimental to (e.g., kills) cells. For a description of these classes of drugs which are known in the art, and their mechanisms of action, see Goodman et al., Goodman and Gilman's The Pharmacological Basis of Therapeutics, 8th Ed., Macmillan Publishing Co., 1990. Additional techniques relevant to the preparation of antibody immunotoxins are provided in for instance Vitetta (1993) and U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232.

A variety of radionuclides are available for the production of radioconjugated antibodies. Examples include, but are not limited to, $^{212}$Bi, $^{131}$I, $^{90}$Y and $^{186}$Re.

Conjugates of the antibody and therapeutic agents are made using a variety of bifunctional protein-coupling agents such as, but not limited to, 4-(4'acetylphenoxy)butanoic acid (AcBut), 3-acetylphenyl acidic acid (AcPac), 4-mercapto-4-methyl-pentanoic acid (Amide), N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene), and derivatives thereof. For example, a ricin immunotoxin can be prepared as described by Vitetta et al. (1987). Carbon-14-labeled 1-isothiocyanatobenzyl-3-methyldiethylene triaminepentaacetic acid (MX-DTPA) is an exemplary chelating agent for conjugation of radionucleotide to the antibody (WO 94/11026).

Immunoglobulin Constructs of the Invention

As used herein, the term "immunoglobulin construct" is intended to refer to constructs in which an antigen binding antibody fragment is linked to a modified ferret IgG Fc region according to the present invention. Of particular interest are immunoglobulin constructs that comprise Fc regions, Fc fusions, and the constant region of the heavy chain (CH1-hinge-CH2*CH*3).

Specific antibody fragments include, but are not limited to (i) the Fab fragment consisting of VL, VH, CL and CH1 domains; (ii) the Fd fragment consisting of the VH and CH1 domains, (iii) the Fv fragment consisting of the VL and VH domains of a single antibody, (iv) the dAb fragment (Ward et al., (1989) Nature 341:544-546) which consists of single variable region (v) isolated CDR regions (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., (1988) Science 242:423-426, Huston et al., (1989) Proc Natl Acad Sci USA 85:5879-5883), (viii) bispecific single chain Fv (WO 03/11161), and (ix) diabodies and triabodies or tetrabodies (Tomlinson et al., (2000) Methods Enzymol 326:461-479; WO 94/13804; Hollinger et al., (1993) Proc Natl Acad Sci USA 90:6444-6448). The molecules may be stabilized by the incorporation of disulphide bridges linking the VH and VL domains (Reiter et al., (1996) nature Biotech 14:1239-1245).

It will be appreciated that the fragments described above (which do not contain a hinge region) may be joined to a hinge-Fc region where the hinge serves as a linker.

In another example, the antibody fragment may be a flex minibody consisting of scFV-CH3 and hinge region sequence (as described in Hu, Shi-zhen et al., (1996) Cancer Research 56:3055-3061).

Antibody Preparation

Antibodies can be prepared using a wide variety of techniques known in the art including the use of hybridoma, recombinant and phage display technologies or a combination thereof. For example monoclonal antibodies can be produced using hybridoma techniques including those known in the art and taught by e.g. Harlow et al., Antibodies: A laboratory Manual (Cold Spring Harbor Laboratory Press 2$^{nd}$ Edn 1988).

The term "monoclonal antibody" as used herein is not limited to antibodies produced through hybridoma technology. The term refers to any antibody that is derived from a single clone, including any prokaryotic, eukaryotic, or phage clone and not the method by which it is produced.

Methods for producing and screening for specific antibodies using hybridoma technology are routine in the art. For example, mice can be immunized with an antigen of interest or a cell expressing such an antigen. Once an immune response is detected, the mouse spleen is harvested and splenocytes isolated. The splenocytes are then fused to myeloma cells. Hybridomas are selected and cloned by limiting dilution. The clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by routine techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete light chain, and the variable region, the CH1 region and the hinge region of the heavy chain.

Antibodies can also be generated using various phage display methods. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labelled antigen or antigen bound or captured to a solid surface or bead. Phage used in these methods are typically filamentous phage, including fd and M13. The antigen binding domains are expressed as a recombinantly fused protein to either the phage gene III or gene VIII protein. Alternatively, the modified FcRn binding portion of immunoglobulins of the present invention can be also expressed in a phage display system. Examples of phage display methods that can be used to make the immunoglobulins, or fragments thereof, of the present invention include those disclosed in Brinkman et al., *J. Immunol. Methods,* 182:41-50, 1995; Ames et al., *J. Immunol. Methods,* 184: 177-186, 1995; Kettleborough et al., *Eur. J. Immunol.,* 24:952-958, 1994; Persic et al., *Gene,* 187:9-18, 1997; Burton et al., *Advances in Immunology,* 57:191-280, 1994; PCT application No. PCT/GB91/01134; PCT publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580, 717; 5,427,908; 5,750,753; 5,821,047; 5,571,698; 5,427, 908; 5,516,637; 5,780,225; 5,658,727; 5,733,743 and 5,969, 108.

After phage selection, the antibody coding regions from the phage can be isolated and used to generate whole antibodies, including human antibodies, or any other desired fragments, and expressed in any desired host, including mammalian cells, insect cells, plant cells, yeast, and bacteria. For example, techniques to recombinantly produce Fab, Fab' and $F(ab')_2$ fragments can also be employed using methods known in the art such as those disclosed in PCT publication WO 92/22324; Mullinax et al., *BioTechniques,* 12(6):864-869, 1992; and Sawai et al., AJRI, 34:26-34, 1995; and Better et al., *Science,* 240:1041-1043, 1988, examples of techniques which can be used to produce single-chain Fvs and antibodies include those described in U.S. Pat. Nos. 4,946,778 and 5,258,498; Huston et al., *Methods in Enzymology,* 203:46-88, 1991; Shu et al., *PNAS,* 90:7995-7999, 1993; and Skerra et al., *Science,* 240:1038-1040, 1988.

Recombinant Production of Antibodies and Immunoglobulin Constructs

The antibodies and immunoglobulin constructs of the present invention can be produced recombinantly. For example, DNA encoding an antibody or antibody construct of the invention is readily isolated and sequenced using conventional procedures (e.g., by using oligonucleotide probes that are capable of binding specifically to genes encoding the heavy and light chains of antibodies). Once isolated, the DNA may be placed into expression vectors, which are then transfected into host cells such as *E. coli* cells, HEK 293 cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al, *Curr. Opinion in Immunol.,* 5:256-262 (1993) and Pluckthun, *Immunol. Revs.,* 130:151-188 (1992). Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, Guide to Molecular Cloning Techniques, Methods in Enzymology volume 152 Academic Press, Inc., San Diego, Calif. (Berger); Sambrook et al. (1989) Molecular Cloning A Laboratory Manual (2nd ed.) Vol. 13, Cold Spring Harbor Laboratory, Cold Spring Harbor Press, N.Y., (Sambrook); and Current Protocols in Molecular Biology, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) Proc. Natl. Acad. Sci. USA 86: 10029 10033.

For recombinant production, the nucleic acid encoding the antibody or antibody construct is preferably isolated and inserted into a replicable vector for further cloning (amplification of the DNA) or for expression. DNA encoding the antibody or antibody construct is readily isolated or synthesized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, a sequence encoding an antibody of the present invention or fragment thereof (e.g., derived from the information provided herein), an enhancer element, a promoter, and a transcription termination sequence.

(i) Signal sequence component. The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader, or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the antibody.

(ii) Promoter component. Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S. D.) sequence operably linked to the DNA encoding the antibody.

Promoters are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2). CMV, bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

(iii) Enhancer element component. Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) Nature 297: 17-18 on enhancing elements for activation of eukaryotic promoters. The enhancer may be spliced into the vector at a position 5' or 3' to the antibody-encoding sequence, but is preferably located at a site 5' from the promoter.

(iv) Transcription termination component. Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/1 1026 and the expression vector disclosed therein.

(v) Selection and transformation of host cells. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus*(mosquito), *Drosophila melanogaster* (fruitfly), and *Bombyx mori* have been identified. A variety of viral strains for transfection are publicly available, e.g., the L-I variant of *Autographa californica* NPV and the Bm-5 strain of *Bombyx mori* NPV, and such viruses may be used as the virus herein according to the present invention, particularly for transfection of *Spodoptera frugiperda* cells.

Examples of useful mammalian host cell lines are monkey kidney CVI line transformed by SV40 (COS-7, ATCC CRL 1651); human embryonic kidney line (293 or 293 cells subcloned for growth in suspension culture, Graham et al. (1977) Gen Virol. 36:59); baby hamster kidney cells (BHK, ATCC CCL 10); Chinese hamster ovary cells (CHO, Urlaub et al., (1980) Proc. Natl. Acad. ScL USA 77:4216); mouse Sertoli cells (TM4, Mather (1980) Biol. Reprod. 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. (1982) Annals N.Y. Acad. Sci. 383:44-68); MRC 5 cells; FS4 cells; and PER.C6™ (Crucell Nev.).

Host cells are transformed with the above-described expression or cloning vectors for antibody or antibody construct production and cultured in conventional nutrient media modified as appropriate for inducing promoters, selecting transformants, or amplifying the genes encoding the desired sequences.

(vii) Culturing the host cells. The host cells used to produce the antibodies of this invention may be cultured in a variety of media. Commercially available media such as Ham's FI0 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. (1979) Meth. Enz. 58:44, Barnes et al., (1980) Anal. Biochem. 102:255, U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Chimeric Antibodies

The antibody according to the invention may be a chimeric antibody.

Chimeric antibodies are made by recombinant means by combining the variable light and heavy chain regions (VL and VH), obtained from antibody producing cells of one species with the constant light and heavy chain regions from another. In a preferred embodiment, chimeric antibodies utilize human variable regions and ferret constant regions, in order to produce an antibody with predominantly ferret domains. The production of chimeric antibodies may be achieved by standard means (as described, e.g., in Morrison, *Science* 229:1202 (1985); Oi et al, *BioTechniques* 4:214 (1986); Gillies et al., (1989) *J. Immunol. Methods* 125:191-202; U.S. Pat. Nos. 5,807,715; 4,816,567 and 4,816,397).

Ferretized and Ferret Antibodies

The term "ferret" antibodies includes antibodies having the amino acid sequence of a ferret immunoglobulin and include antibodies isolated from ferret immunoglobulin libraries or from animals transgenic for one or more ferret immunoglobulins.

The antibodies of the present invention may be 'ferretized' antibodies. Ferretized forms of non-ferret (e.g., human) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-ferret immunoglobulin. Ferretized antibodies include ferret immunoglobulins (recipient antibody) in which residues from a complementary determining region (CDR) of the recipient are replaced by residues from a CDR of a non-ferret species (donor antibody) such as human having the desired specificity, affinity and capacity. In some instances, one or more Fv framework residues of the ferret immunoglobulin are replaced by corresponding non-ferret residues. Ferretized antibodies may also comprise residues which are found neither in the recipient antibody nor in the imported CDR or framework sequences. In general, the ferretized antibody will comprise substantially all of at least one, and typically two, variable domains, in which all or substantially all of the CDR regions correspond to those of a non-ferret immunoglobulin and all or substantially all of the FR regions are those of a ferret immunoglobulin consensus sequence. The ferretized antibody optimally also will comprise at least a portion of an immunoglobulin constant region (Fc), typically that of a ferret immunoglobulin.

Methods for ferretizing non-ferret antibodies can be essentially performed following the method of Winter and co-workers (Jones P T et al (1986) Nature 321(6069):522; Riechmann L et al (1988) Nature 332(6162):323-327; Verhoeyen M et al (1988) Science 239(4847):1534-1536. Generally, a ferretized antibody has one or more amino acid residues introduced into it from a source which is non-ferret. These non-ferret amino acid residues are often referred to as "import" residues, which are typically taken from an "import" variable domain. Accordingly, such "ferretized" antibodies are chimeric antibodies (U.S. Pat. No. 4,816,567), wherein substantially less than an intact human variable domain has been substituted by the corresponding sequence from a non-ferret species.

Antibodies can be ferretized using a variety of techniques known in the art including, for example, CDR-grafting (EP 239400; PCT publication WO 91/09967; U.S. Pat. Nos. 5,225,539; 5,530,101; and 5,585,089), veneering or resurfacing (EP 592106; EP519596; Padlan E A v al (1991) Mol Immunol 28(4-5):489; Studnicka G M et al (1994) Protein Eng 7(6):805-14) and chain shuffling (U.S. Pat. No. 5,565,332).

In some instances residues within the framework regions of one or more variable regions of the ferret immunoglobulin are replaced by corresponding non-ferret residues. Also included within the scope of the invention are "ferret veneered antibodies". The term ferret veneered antibody refers to selective replacement of framework region residues with ferret framework region residues in order to provide a xenogenic molecule comprising an antigen-binding site which retains substantially all of the native framework region folding structure. Veneering techniques are based on the understanding that the ligand-binding characteristics of an antigen-binding site are determined primarily by the structure and relative disposition of the heavy and light chain CDR sets within the antigen-binding surface. By using veneering techniques, exterior (e.g. solvent accessible) framework region residues, which are readily encountered by the immune system, are selectively replaced with ferret residues to provide a hybrid molecule that comprises either a weakly immunogenic, or substantially non-immunogenic, veneered surface.

Antibody Binding

The antibodies of the invention may be assayed for specific binding by any method known in the art. The immunoassays which can be used include but are not limited to competitive and non-competitive assay systems using techniques such as BIAcore analysis, FACS (Fluorescent Activated Cell Sorter) analysis, immunofluorescence, immunocytochemistry, western blots, radioimmunoassays, ELISA, sandwich immunoassays, immunoprecitation assays, precipitin reactions, gel diffusion precipitin reactions, immunodiffusion assays, agglutination assays, complement-fixation assays, immunoradiometric assays, fluorescent immunoassays, protein A immunoassays etc.

Immunoglobulin Fusion Proteins

The present invention also provides fusion proteins comprising a bioactive molecule recombinantly fused or chemically conjugated (including covalent or non-covalent conjugations) to a modified ferret lgG Fc region. The term fusion protein is often synonymous with the term "immunoadhesin." Without wishing to be bound by theory, it is believed that mutations in the Fc region increase the affinity for ferret FcRn. In a particular embodiment, the fusion protein comprises the amino acid sequence in SEQ ID NO: 1, or a variant thereof.

The bioactive molecule which is fused can be any polypeptide or synthetic drug known to one of skill in the art. Examples of suitable polypeptides include cytokines, cell adhesion molecules (e.g. CTLA4, CD2 and CD28), ligands (e.g. TNF-alpha, TNF-beta and anti-angiogenic factor), receptors and growth factors (e.g. PDGF, EGF, NGF and KGF), an enzyme, a chemokine, The bioactive molecule which can be fused may also be a nonproteinaceous polymer e.g. polyethylene glycol or polypropylene glycol.

Methods for producing the bioactive molecule or immunoglobulin fusion proteins of the invention include standard recombinant techniques or protein synthetic techniques e.g. by use of an automated protein synthesizer. For example, a nucleic acid molecule encoding the bioactive molecule of the invention can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence. Moreover, a nucleic acid sequence encoding a molecule can be cloned into an expression vector containing the ferret Fc region such that the molecule is linked in frame to the Fc region.

Methods for fusing or conjugating polypeptides to the constant regions of antibodies are known in the art (see for example, U.S. Pat. No. 5,336,603, U.S. Pat. No. 5,622,929, U.S. Pat. No. 5,359,046, U.S. Pat. No. 5,349,053, U.S. Pat. No. 5,447,851, U.S. Pat. No. 5,723,125, U.S. Pat. No. 5,783,181, U.S. Pat. No. 5,908,626, U.S. Pat. No. 5,844,096, U.S. Pat. No. 5,112,946, U.S. Pat. No. 7,955,590).

The nucleotide sequence encoding the bioactive molecule may be obtained for example from Genbank, and the nucleotide sequence encoding a constant domain may be determined by sequence analysis of mutants produced using techniques described herein. The nucleotide sequence encoding the fusion protein can be inserted into an appropriate expression vector.

Polynucleotides

The present invention also provides polynucleotides comprising a nucleotide sequence encoding the modified antibody or antibody construct of the invention and polynucleotide sequences that hybridize under high stringency thereto.

Assays for Half-Life of Antibodies or Immunoglobulin Constructs of the Invention The half-life of the antibodies or immunoglobulin constructs of the invention can be measured by pharmacokinetic studies (PK) according to the method described by Kim et al, Eur J of Immunol 24:542 (1994). According to this method radiolabelled modified immunoglobulin is injected intravenously into ferrets and its plasma concentration is periodically measured as a function of time, for example at 2 to 504 hours after the injection. The clearance curve thus obtained should be biphasic, that is, an alpha phase and beta phase. For the determination of the in vivo half-life of the modified antibody or antibody construct of the invention, the clearance rate in beta-phase is calculated and compared with that of the wild type or unmodified antibody or immunoglobulin construct.

It has recently been reported that enhanced antibody half-life can be correlated with improved in vivo activity (Zalevsky J et al., (2010) nature Biotechnology 28(2):157-159).

In order to compare the ability of the unmodified antibody or antibody construct to bind ferret FcRn with that of modified antibody or antibody construct comprising heavy chain constant region modifications, each antibody molecule can be radio-labelled and reacted with FcRn-expressing cells in vitro. The radioactivity of the cell-bound fractions can then be counted and compared. The cells expressing FcRn used in this assay are preferably mammalian cells which express recombinant soluble ferret FcRn. After counting the radioactivity of the bound fraction of modified antibody or antibody construct or that of unmodified antibody or antibody construct, the bound molecules can then be extracted with detergent and the percent release per unit number of cells can be calculated and compared.

Affinity of modified antibody, immunoglobulin construct or immunoglobulin fusion for FcRn can be measured by surface Plasmon resonance (SPR) measurement using, for example, a Proteon XPR36 protein interaction array system (BioRad, Hecrule, Calif.) as described. In this method, FcRn molecules are coupled to a GLC sensor chip using ammine coupling and the binding of modified antibody or antibody construct to the immobilized FcRn is measured at a certain flow rate to obtain sensorgrams using Proteon Manager software, based on which on- and off rates of the modified antibody or antibody construct to FcRn can be calculated.

Use of Modified Antibodies or Immunoglobulin Constructs of the Invention

The modified antibodies or immunoglobulin constructs in the present invention can be used for various non-therapeutic purposes. They may be used as an affinity purification agent. They may also be useful in diagnostic assays, such as detecting expression of an antigen of interest in specific cells, tissues, or serum. For diagnostic applications, the antibodies typically will be labeled with a detectable moiety, including radioisotopes, fluorescent labels, and various enzyme substrate labels. The antibodies may also be employed in any known assay method, such as competitive binding assays, direct and indirect sandwich assays, and immunoprecipitation assays. The antibodies or immunoglobulin constructs may also be used for in vivo diagnostic assays. Generally, the antibodies or immunoglobulin constructs are labeled with a radionucleotide so that the antigen or cell expressing it can be localized using immunoscintigraphy.

All references or documents referred to herein are considered to be incorporated by reference in their entirety.

Throughout this specification the word “comprise”, or variations such as “comprises” or “comprising”, will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

EXAMPLES

Example 1

Pharmacokinetics and Immune Responses after a Single Dose of Human mAb

Figure 1B:
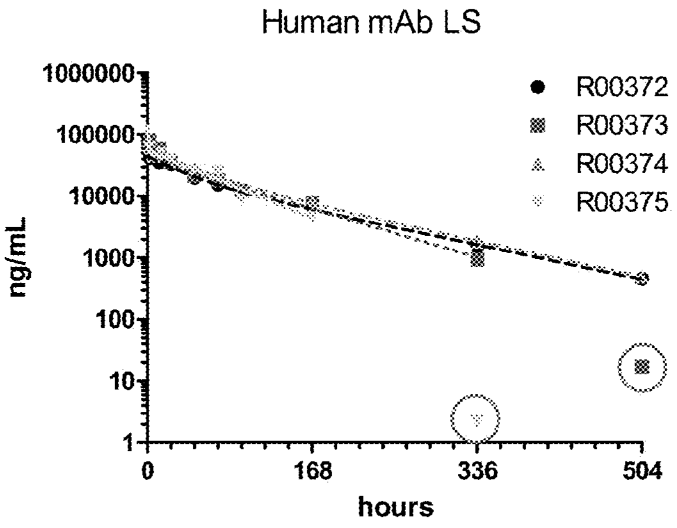
Figure 2:
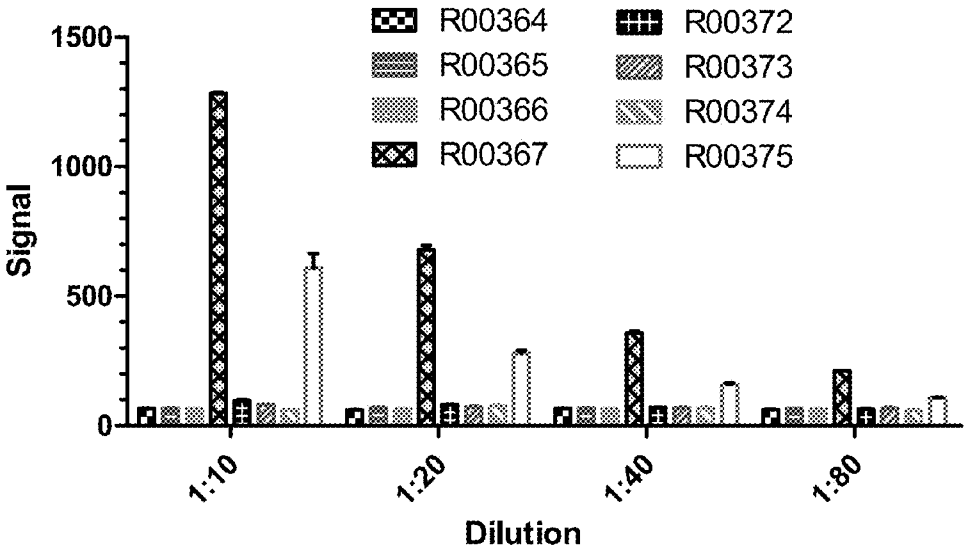
FIG. 2. Immune response. Bars represent the relative amounts of ferret anti-human mAb antibodies present in plasma samples from ferrets given either WT human mAb (R364-R367) or an LS mutant (R372-R375) taken 504 hours after injection.

Initial efforts were focused on determining the PK of a human IgG antibody in ferrets and testing for the induction of polyclonal ferret anti-human IgG antibodies (commonly referred to as anti-drug antibodies or ADA). For this study, male ferrets were intravenously injected with a single 2 mg/kg dose of a human IgG1 mAb that was expected to not bind to any ferret antigens (specific for RSV F-glycoprotein). Blood samples were then collected 2, 6, 12, 24, 48, 72, 96, 168, 336 and 504 hours after injection and plasma prepared from each sample. In addition to the WT mAb, a second mAb containing the half-life extending substitutions, M428L & N434S (LS) was also tested. Concentrations of human mAb in the plasma samples were determined using an electrochemiluminescent assay. Of the eight animals in this study, two experienced an acute drop in test mAb concentration resulting in values that were identified as outliers using the Grubbs test (FIG. 1). Ferret anti-human mAb antibodies were detected in one of the two ferrets, R375, using a bridging assay (FIG. 2). The negative result observed for the other outlier, R373, may have been due to residual human mAb test article in the plasma sample inhibiting binding of ferret antibodies to the immobilized human mAb on the assay plate. ADA were detected in one additional ferret, R367, which experienced a drop in mAb concentration that did not reach significance ($p<0.05$) in the Grubbs outlier test. Excluding these three time points, the average half-life of the WT human IgG was 31±10 hours whereas the half-life of the LS variant averaged 72±21 hours. Despite the extended half-life of the LS variant, the detection of anti-human mAbs prompted preparation of a chimeric mAb with human variable regions and ferret constant regions.

Example 2

Cloning of Ferret IgG Constant Region Sequences

Because the amino acid sequences of the ferret IgG constant regions were only partially known, cDNAs encoding the complete constant regions for the ferret IgG heavy chain and light chain were cloned. This was done using RNA isolated from ferret kidney, lung, liver or spleen, and DNA primers designed based on the partial ferret sequence and the mink sequences available in public databases. The ferret DNA sequences were reverse-transcribed, PCR-amplified, and sequenced. Three amino acid sequence differences were found between the consensus ferret HC sequence and the partial database sequence (Genbank Accession Number EZ459103) suggesting that the ferret may have multiple IgG isotypes. All of the differences were in a region that aligned with the hinge region of human IgG1. The ferret HC constant region sequence (SEQ ID NO. 1) was 89% identical to the mink sequence with most of the differences again occurring in the hinge region (FIG. 3). It should be noted that the first six amino acids of the cloned ferret HC sequence were derived from a primer based on the mink sequence, and therefore the possibility exists that one or more of the first six amino acids do not match the endogenous ferret sequence. The cloned ferret LC sequence (SEQ ID NO. 3) was identical to the partial sequence found in the database (Genbank Accession Number EZ457190) and shared 94% identity with the mink sequence.

Example 3

Preparation of Chimeric Ferret/Human Antibodies

Figure 4:
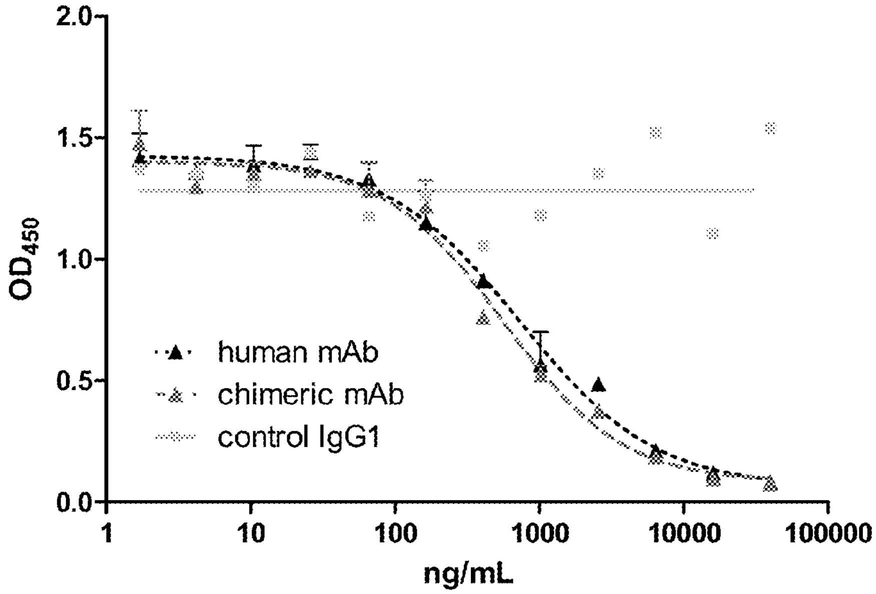
FIG. 4. Competition binding to RSV F glycoprotein. A non-linear equation was used to fit a line to the data points and calculate $IC_{50}$.
Figure 5:
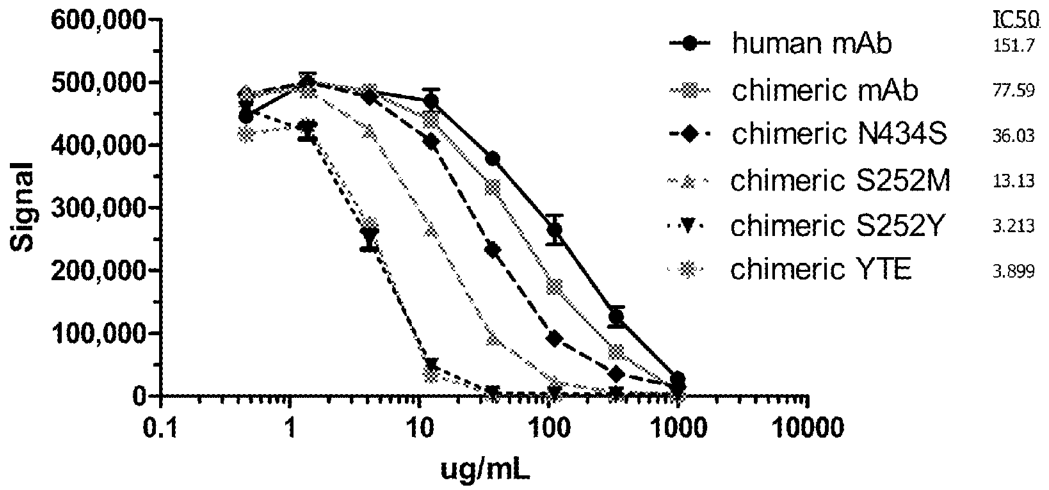
FIG. 5. Ferret FcRn binding. The binding of human and chimeric mAbs to ferret FcRn at pH 6.0 was measured in a competition format.

To prepare chimeric mAbs for testing, variable regions from a human anti-RSV mAb were used because they would not be expected to bind endogenous ferret proteins, which could affect pharmacokinetics. Expression plasmids were prepared by splicing the anti-RSV variable regions upstream of the newly-cloned ferret IgG constant regions. In addition, amino acid substitutions which have been shown to extend the half-life of human antibodies were introduced into the ferret Fc. The position given for these substitutions is from application of the human antibody EU numbering system to the ferret sequence based on homology. Specifically, variants were made in which the serine at position 252 was replaced either with a methionine (S252M), the amino acid found in human IgG, or a tyrosine (S252Y). A third variant combined the S252Y substitution with two other substitutions: S254T and T256E (YTE) to create a triple mutant. A fourth variant substituted the asparagine at position 428 with serine (N434S). The WT chimeric mAb and the four variants were expressed transiently in HEK293E cells. Protein A and protein G columns aligned in series were used in purification. Initially, protein G was used based on work by Martel and Aasted who first reported the purification of ferret antibodies, but after ferret mAb was detected in the protein G column flow-through, a protein A column was added to improve capture of the ferret antibodies. The purified antibodies were analyzed by SDS-PAGE under denaturing and both reducing and non-reducing conditions and the banding patterns were consistent with the expected sizes of the fully-assembled mAbs and individual HCs and LCs. SE-HPLC chromatograms showed a single, sharp peak characteristic of a homogenous, monodisperse mAb (data not shown). To access structural integrity, the WT chimeric mAb was tested for binding to its antigen, RSV F glycoprotein, in a competition assay format (FIG. 4). The calculated $IC_{50}$ values were 736±156 ng/mL and 565±105 ng/mL for the human and chimeric mAbs, respectively, demonstrating that the structure of the human variable regions was functionally intact when expressed with ferret constant regions.

Example 4

Cloning and Expression of Soluble Ferret FcRn

FcRn receptor binding is commonly used to evaluate antibodies engineered to have an extended half-life. FcRn is made up of an alpha and a beta chain, yet a search of public databases revealed only the ferret beta chain sequence, also known as β2-microglobulin (β2M). To clone DNA encoding the ferret alpha chain (SEQ ID NO. 5), oligonucleotide primers were designed based on the alignment of known sequences from several species. Using RNA from ferret tissues, PCR amplicons were generated and then sequenced. The consensus sequence shared 92% identity with the dog FcRn alpha chain, the closest relative whose sequence was known. The Fc-binding portion of the cloned alpha chain was then expressed with ferret β2M in HEK293 cells to generate soluble ferret FcRn (sFcRn). Following purification, the purified FcRn was analyzed by SDS-PAGE under reducing and non-reducing conditions (Data not shown). Two bands were seen migrating near the expected molecular weight of the alpha chain, 30.1 kDa, and a single band near the expected molecular weight of the beta chain, 11.5 kDa. The doublet may have been due to glycosylation heterogeneity as the ferret alpha chain contains two N-linked glycosylation motifs and multiple glycoforms have been observed with FcRn from other species.

Example 5

Chimeric mAb Binding to Ferret FcRn

The human/ferret chimeric mAbs were tested for binding to ferret FcRn (SEQ ID NO:8) at pH 6.0 to mimic conditions in the endosomes where IgG-FcRn binding occurs. This competitive binding assay used AlphaScreen technology in which the proximity-dependent transfer of singlet oxygen from the donor beads to acceptor beads upon excitation can be detected. For this, WT chimeric mAb was captured on streptavidin-coated donor beads and His-tagged ferret FcRn was captured on nickel-coated acceptor beads Inhibition of the interaction between the donor and acceptor beads by test mAbs in solution was then measured. The test mAbs were titrated and the resulting inhibition curves used to calculate $IC_{50}$ values. The $IC_{50}$ values for the human and chimeric mAbs were 152 and 78 μg/mL, respectively. This 2-fold difference indicated that, even without additional Fc engineering, human/ferret chimeric mAbs might have a longer half-life than human mAbs. All four of the variants gave $IC_{50}$ values that were lower than the WT chimeric mAb, indicating stronger ferret FcRn binding. The largest improvements were seen when the serine at position 252 was mutated. Changing this amino acid to a methionine, as found in the human sequence, resulted in an $IC_{50}$ of 13 ug/mL and mutating it to a tyrosine reduced the $IC_{50}$ to 3.2 ug/mL, a 24-fold improvement over wild-type. The YTE variant, which added two mutations in addition to S252Y, did not show additional improvement beyond S252Y by itself.

Surface plasmon resonance was also used to measure the binding of variants to ferret FcRn at pH 6. For this analysis, ferret FcRn was covalently immobilized and the antibodies were in solution. The calculated Kd values paralleled the results of the AlphaScreen assay. Compared to WT, the S252M substitution increased binding affinity 6-fold (from 930 nM to 149 nM) and the S252Y substitution increased affinity 50-fold (to 20 nM).

Example 6

Pharmacokinetics of Chimeric mAb Variants in Ferrets

The pharmacokinetics of the WT chimeric mAb and the S252M, S252Y and YTE variants were evaluated in ferrets. Male ferrets were intravenously-injected with a 2 mg/kg dose of mAb. Blood samples were then collected 2, 6, 12, 24, 48, 72, 96, 168, 336 and 504 hours after injection and plasma prepared from each sample. Each ferret was given a second injection of test article after the last sampling and blood samples collected at the same time points relative to the second injection. Concentrations of human mAb in the plasma samples were measured using the previously-described electrochemiluminescent assay. The average half-lives of the S252M, S252Y and YTE variants were 127±38, 206±44, and 213±28 hours, respectively. All three showed an extended half-life compared to WT chimeric mAb with a half-life of 65±27 hours. FIGS. 6A-6D show the mAb concentrations determined for individual ferrets after the first injection. Results from two of the ferrets, one in the in the S252M group and another in the S252Y group, are not shown because technical difficulties with the vasculature access port prevented sample collection. mAb concentrations were unusually variable in plasma samples from four ferrets given WT chimeric mAb, with calculated half-life values ranging from 36 hours to 100 hours. The mAb concentrations in the plasma samples from ferrets given the three variants were more consistent.

FIGS. 7A-7D show mAb concentrations in plasma samples taken after the second dose and Table 2 gives a comparison of half-lives determined from samples taken after the first and second doses. Overall, the half-lives were similar to what was observed for the first injection, with a trend toward longer half-life after the second dose. Importantly, what was not seen in any of the ferrets was an abrupt decrease in chimeric mAb concentration that would be suggestive of an ADA response.

TABLE 2

Comparison of half-lives after the first and second doses. The half-lives of the human/ferret chimeric mAbs were individually calculated based on samples taken after the first or second dose. A decrease in half-life after the second dose might indicate an immune response. The percent difference between the first and second dose is given with a positive number indicating an increased half-life after the second dose and a negative number indicating a decreased half-life.

| test article | animal number | 1st dose $T_{1/2}$ (hours) | 2nd dose $T_{1/2}$ (hours) | % difference |
|---|---|---|---|---|
| chimeric mAb | 388 | 100 | 89 | −11% |
| | 389 | 36 | 45 | +23% |
| | 390 | 55 | 67 | +22% |
| | 391 | 69 | 83 | +21% |
| chimeric YTE | 392 | 204 | 184 | −10% |
| | 393 | 271 | 276 | +2% |
| | 394 | 214 | 254 | +18% |
| | 395 | 165 | 156 | −5% |
| chimeric S252M | 396 | 171 | 184 | +8% |
| | 397 | 102 | 139 | +37% |
| | 398 | nd | nd | nd |
| | 399 | 108 | 132 | +22% |
| chimeric S252Y | 400 | 185 | 248 | +34% |
| | 401 | nd | 165 | nd |
| | 402 | 196 | 279 | +42% |
| | 403 | 238 | 273 | +15% |

The notation "nd" indicates that data was not available due to technical issues.

In an attempt to confirm that detectable ADAs were not generated against the chimeric mAbs, a bridging assay similar to the one used with the human mAbs was used to analyze plasma samples. No ADAs were detected in the final plasma samples, taken 504 hours after the 2nd dose (data not shown). A shortcoming of this assay format was the potential for false negative results due to residual test article in the plasma samples. For this reason, a control anti-idiotype mAb against the variable regions of the chimeric mAbs was used as a surrogate ADA to determine if residual chimeric mAb in the plasma would block the ADAs from bridging between the labeled chimeric mAb on the plate and the labeled mAb in solution. The anti-idiotype mAb (representing surrogate ADA) was spiked into the 504 hour plasma samples and then those samples tested in the same assay. Detection of the anti-idiotype mAb at a concentration of 1 μg/mL was partially inhibited in the 504 hour plasma samples, and when the concentration was reduced to 0.1 μg/mL, its detection was completely inhibited in most of the plasma samples (data not shown). Detection was not inhibited when it was added to control ferret plasma. These results suggested that residual chimeric mAb still present in the plasma samples could interfere with detection of ADA. Consistent with this notion, the plasma samples with the lowest concentration of residual chimeric mAb showed the least inhibition when assaying for the anti-idotype mAb. Therefore, while the consistent rate of clearance over time observed for the human/ferret chimeric mAbs suggests a lack of ADA response, it was unable to be confirmed through direct testing.

SEQUENCE LISTING

| SEQ ID NO: | Type | Species | Description | Sequence |
| --- | --- | --- | --- | --- |
| 1 | PRT | ferret | Heavy Chain-Fc Wild-type | ASTTAPSVFPLAPSCGATPGSTVALACLVSGYFP<br>EPVTVSWNSGSLTSGVHTFPSVLQSSGLYSLSSM<br>VTVPSSRWPSDTFICTVAHPASNTKVDKRVTQG<br>GPPHTDPCKKCPQPPACDMLGGPSVFMFPPKPK<br>DTLSISRTPEVTCMVVDLEDPEVQISWFVDNQE<br>VHAAKTNSREQQFNSTFRVVSVLPIQHQDWLKG<br>KVFKCKVNNKALPSPIERTISKARGEPHQPSVYV<br>LPPPRDEMSRTTISVTCLVKDFYPPDIDVEWQSN<br>GRQLPEASVRTTPPQLDADGSYFLYSKLSVDKA<br>HWQRGDTFTCAVLHEALHNHHTQKSISQSPGK* |
| 2 | PRT | ferret | Heavy Chain-Fc S252Y | ASTTAPSVFPLAPSCGATPGSTVALACLVSGYFP<br>EPVTVSWNSGSLTSGVHTFPSVLQSSGLYSLSSM<br>VTVPSSRWPSDTFICTVAHPASNTKVDKRVTQG<br>GPPHTDPCKKCPQPPACDMLGGPSVFMFPPKPK<br>DTLYISRTPEVTCMVVDLEDPEVQISWFVDNQE<br>VHAAKTNSREQQFNSTFRVVSVLPIQHQDWLKG<br>KVFKCKVNNKALPSPIERTISKARGEPHQPSVYV<br>LPPPRDEMSRTTISVTCLVKDFYPPDIDVEWQSN<br>GRQLPEASVRTTPPQLDADGSYFLYSKLSVDKA<br>HWQRGDTFTCAVLHEALHNHHTQKSISQSPGK* |
| 3 | PRT | ferret | Heavy Chain-Fc S252M | ASTTAPSVFPLAPSCGATPGSTVALACLVSGYFP<br>EPVTVSWNSGSLTSGVHTFPSVLQSSGLYSLSSM<br>VTVPSSRWPSDTFICTVAHPASNTKVDKRVTQG<br>GPPHTDPCKKCPQPPACDMLGGPSVFMFPPKPK<br>DTLMISRTPEVTCMVVDLEDPEVQISWFVDNQE<br>VHAAKTNSREQQFNSTFRVVSVLPIQHQDWLKG<br>KVFKCKVNNKALPSPIERTISKARGEPHQPSVYV<br>LPPPRDEMSRTTISVTCLVKDFYPPDIDVEWQSN<br>GRQLPEASVRTTPPQLDADGSYFLYSKLSVDKA<br>HWQRGDTFTCAVLHEALHNHHTQKSISQSPGK* |
| 4 | PRT | ferret | Heavy Chain-Fc YTE | ASTTAPSVFPLAPSCGATPGSTVALACLVSGYFP<br>EPVTVSWNSGSLTSGVHTFPSVLQSSGLYSLSSM<br>VTVPSSRWPSDTFICTVAHPASNTKVDKRVTQG<br>GPPHTDPCKKCPQPPACDMLGGPSVFMFPPKPK<br>DTLYITREPEVTCMVVDLEDPEVQISWFVDNQE<br>VHAAKTNSREQQFNSTFRVVSVLPIQHQDWLKG<br>KVFKCKVNNKALPSPIERTISKARGEPHQPSVYV<br>LPPPRDEMSRTTISVTCLVKDFYPPDIDVEWQSN<br>GRQLPEASVRTTPPQLDADGSYFLYSKLSVDKA<br>HWQRGDTFTCAVLHEALHNHHTQKSISQSPGK* |
| 5 | PRT | ferret | Light Chain-Fc | NDAQPSVFLFQPSPDQLHTGSASVVCMLNGFYP<br>REVNVKWKVDGVTKNTGILESVTEQDSKDSTY<br>SLSSTLTMPSTEYLSHEKYSCEVTHKSLSSPLVK<br>SFQRSECQ* |
| 6 | DNA | ferret | Heavy Chain-Fc | GCTTCCACCACGGCCCCATCGGTTTTCCCACT<br>GGCCCCCAGCTGCGGGGCCACCCCCGGATCC<br>ACAGTGGCCCTGGCCTGCCTGGTGTCCGGCTA<br>CTTCCCTGAGCCTGTCACTGTGTCCTGGAACT<br>CCGGCTCCTTGACCAGCGGTGTGCACACCTTC<br>CCGTCTGTCCTGCAGTCCTCGGGCCTCTACTC<br>TCTCAGCAGCATGGTGACCGTGCCCTCCAGCA<br>GGTGGCCCAGCGACACCTTCATCTGCACCGT<br>GGCCCACCCAGCCAGTAACACCAAGGTGGAC<br>AAGAGAGTGACCCAAGGAGGACCTCCTCACA<br>CTGACCCATGCAAAAAATGTCCCCAACCTCCA<br>GCATGTGATATGCTCGGAGGACCTTCAGTCT<br>TCATGTTCCCCCCGAAACCCAAGGACACCCTC<br>TCCATTTCCCGAACCCCCGAGGTTACATGCA<br>TGGTGGTGGACCTGGAAGACCCTGAGGTCCA<br>GATCAGCTGGTTTGTGGACAACCAGGAGGTG<br>CACGCGGCCAAGACGAATTCGCGTGAGCAGC<br>AGTTCAACAGCACCTTCCGTGTGGTCAGTGTC<br>CTCCCCATCCAGCACCAGGACTGGCTCAAGGG<br>GAAGGTCTTCAAGTGCAAGGTCAACAACAA<br>AGCTCTCCCATCCCCCATTGAGAGGACCATCT<br>CCAAGGCCAGAGGGGAACCCCATCAGCCCA<br>GTGTGTATGTCCTGCCCCCACCCCGGGACGAG<br>ATGAGCAGGACCACCATCAGTGTGACCTGCC<br>TGGTCAAAGACTTCTACCCACCTGACATCGAT<br>GTGGAGTGGCAGAGCAACGGCCGTCAGTTAC |

-continued

SEQUENCE LISTING

| SEQ ID NO: | Type | Species | Description | Sequence |
|---|---|---|---|---|
| | | | | CAGAGGCCAGTGTCCGAACAACCCCGCCCCA GCTGGATGCGGACGGCAGCTACTTCCTCTACA GCAAGCTCTCCGTGGACAAGGCGCACTGGCA GCGGGGAGACACCTTCACGTGTGCGGTGCTG CATGAAGCCCTACACAACCATCACACGCAGA AGTCCATCTCCCAGTCTCCGGGTAAATGA |
| 7 | DNA | ferret | Light Chain-Fc | AATGATGCCCAGCCATCCGTCTTTCTGTTCCA ACCATCTCCGGACCAGTTACATACCGGCAGT GCCTCTGTCGTGTGCATGCTGAATGGCTTCTA CCCCAGAGAAGTCAATGTCAAATGGAAGGTT GATGGTGTTACCAAAAACACAGGCATCCTGG AAAGTGTCACAGAACAAGACAGCAAGGACAG CACCTACAGCCTCAGCAGCACCTTGACGATGC CCAGTACGGAGTACCTAAGTCATGAGAAGT ACTCCTGTGAGGTCACTCACAAGAGCCTGTCC TCCCCTCTTGTCAAGAGCTTCCAAAGGAGCG AGTGCCAATGA |
| 8 | PRT | ferret | soluble FcRn | MGVPRPRSWGLGFLLFLLPTVRAESNLSLLYHL TAVSSPAPGAPAFWVSGWLGPQQYLSYNNLRA EAEPCGAWVWENQVSWYWEKETTDLRSKQEL FLEGLKALGKGGPYTLQGLLGCELGPDNASVPV AKFALNGEDFMTFDPKLGTWDGDWPETETIQK TWMQHAGAVSKERTFLLNSCPQRLLGHLERGR GNLEWKEPPSMRLKARPGSPGFSVLTCSAFSFYP PELQLRFLRNGLAVGSGEGDFGPNGDGSFHAWS SLTVKSGDEHHYRCVVQHAGLPQPLTVELESPA RSS |

We claim:

1. An isolated antibody, comprising a ferret IgG Fc region modified relative to a corresponding unmodified ferret IgG Fc region wherein the ferret IgG Fc region comprises a substitution at amino acid residue 252 selected from S252Y or S252M and substitutions S254T and T256E numbered according to the EU index as in Kabat, wherein the in vivo half-life of the modified antibody, is increased by about 2 fold to about 3.5 fold in a ferret compared with the corresponding unmodified antibody.

2. The antibody according to claim 1, wherein the antibody is a chimeric, ferret, ferretized, or a ferret veneered antibody.

3. The antibody according to claim 1, wherein the antibody specifically binds to Respiratory Syncytial Virus F glycoprotein.

4. The antibody according to claim 3, comprising a heavy chain constant region sequence set forth in one of SEQ ID NOs: 1-4.

5. The antibody according to claim 3, further comprising a light chain constant region sequence set forth in SEQ ID NO: 5.

6. An isolated antibody comprising:

a. a human or humanized Fab, and b. a ferret IgG Fc region modified relative to a corresponding unmodified ferret IgG Fc region wherein the ferret IgG Fc region comprises a substitution at amino acid residue 252 selected from S252Y or S252M and substitutions S254T and T256E numbered according to the EU index as in Kabat, wherein the in vivo half-life of the modified antibody is increased by about 2 fold to about 3.5 fold in a ferret compared with the corresponding unmodified antibody.

* * * * *